United States Patent
Kusumoto et al.

(10) Patent No.: US 9,688,787 B2
(45) Date of Patent: Jun. 27, 2017

(54) POLYMERIZABLE COMPOUND HAVING LATERAL SUBSTITUENT IN TERMINAL RING STRUCTURE

(71) Applicant: DIC CORPORATION, Tokyo (JP)

(72) Inventors: Tetsuo Kusumoto, Kita-adachi-gun (JP); Masahiro Horiguchi, Kita-adachi-gun (JP); Takashi Matsumoto, Kita-adachi-gun (JP); Yoshio Aoki, Kitaadachi-gun (JP); Masanao Hayashi, Kita-adachi-gun (JP); Masayuki Iwakubo, Kitaadachi-gun (JP)

(73) Assignee: DIC CORPORATION, Tokyo (JP)

( * ) Notice: Subject to any disclaimer, the term of this patent is extended or adjusted under 35 U.S.C. 154(b) by 0 days.

(21) Appl. No.: 14/826,630

(22) Filed: Aug. 14, 2015

(65) Prior Publication Data

US 2015/0361190 A1 Dec. 17, 2015

Related U.S. Application Data

(63) Continuation of application No. 14/007,242, filed as application No. PCT/JP2012/059342 on Apr. 5, 2012, now Pat. No. 9,120,883.

(30) Foreign Application Priority Data

Apr. 18, 2011 (JP) ................. 2011-092027

(51) Int. Cl.
| | |
|---|---|
| *C08F 22/20* | (2006.01) |
| *C07C 69/92* | (2006.01) |
| *C07C 69/94* | (2006.01) |
| *C09K 19/38* | (2006.01) |
| *C09K 19/20* | (2006.01) |
| *C09K 19/32* | (2006.01) |
| *C07C 69/78* | (2006.01) |
| *C09K 19/34* | (2006.01) |
| *C09K 19/04* | (2006.01) |

(52) U.S. Cl.
CPC ............. *C08F 22/20* (2013.01); *C07C 69/78* (2013.01); *C07C 69/92* (2013.01); *C07C 69/94* (2013.01); *C09K 19/2007* (2013.01); *C09K 19/321* (2013.01); *C09K 19/322* (2013.01); *C09K 19/3814* (2013.01); *C09K 19/3411* (2013.01); *C09K 2019/0448* (2013.01); *C09K 2019/325* (2013.01); *C09K 2019/326* (2013.01); *C09K 2019/3413* (2013.01); *C09K 2019/3416* (2013.01)

(58) Field of Classification Search
CPC ......... C07C 69/78; C07C 69/92; C07C 69/94; C08F 22/20; C09K 19/2007; C09K 19/321; C09K 19/322; C09K 19/3814; C09K 19/3411; C09K 2019/0448; C09K 2019/325; C09K 2019/326; C09K 2019/3413; C09K 2019/3416
USPC ................... 560/73, 100; 526/280
See application file for complete search history.

(56) References Cited

U.S. PATENT DOCUMENTS

| | | | |
|---|---|---|---|
| 5,190,689 A | 3/1993 | Finkelmann et al. | |
| 5,273,680 A | 12/1993 | Gray et al. | |
| 5,397,505 A | 3/1995 | Rienger et al. | |
| 6,291,035 B1 * | 9/2001 | Verrall | G02B 5/3016 349/117 |
| 6,491,990 B1 * | 12/2002 | Parri | C09K 19/2007 252/299.64 |
| 2008/0143943 A1 * | 6/2008 | May | C09K 19/18 349/117 |

FOREIGN PATENT DOCUMENTS

| | | |
|---|---|---|
| CN | 101393358 A | 3/2009 |
| EP | 1786887 B1 | 7/2008 |
| GB | 2280445 A | 2/1995 |
| JP | 62-74987 A | 4/1987 |
| JP | 11-116512 A | 4/1999 |
| JP | 2000-186283 A | 7/2000 |
| JP | 2003-129054 A | 5/2003 |
| JP | 2008-088291 A | 4/2008 |
| JP | 2008-195762 A | 8/2008 |

OTHER PUBLICATIONS

International Search Report for PCT/JP2012/059342, Mailing Date of Jun. 12, 2012.

* cited by examiner

*Primary Examiner* — Ling Choi
*Assistant Examiner* — Chun-Cheng Wang
(74) *Attorney, Agent, or Firm* — Westerman, Hattori, Daniels & Adrian, LLP

(57) ABSTRACT

An object of the invention is to provide a polymerizable compound having small refractive index anisotropy and having high storage stability and high alignment properties when constituting a polymerizable liquid crystal composition, and provide a polymerizable liquid crystal composition containing the polymerizable compound. Further, the object is to provide a polymer produced by polymerizing the polymerizable liquid crystal composition and an optically anisotropic body including the polymer. The present invention provides a polymerizable compound represented by general formula (I), a polymerizable liquid crystal composition containing the compound as a constituent component, and further provides a polymer produced by polymerizing the polymerizable liquid crystal composition and an optically anisotropic body including the polymer.

7 Claims, No Drawings

POLYMERIZABLE COMPOUND HAVING LATERAL SUBSTITUENT IN TERMINAL RING STRUCTURE

CROSS-REFERENCE TO RELATED APPLICATION

This application is a continuation of U.S. application Ser. No. 14/007,242, filed on Sep. 24, 2013, which is a 371 of International Application No. PCT/JP2012/059342, filed on Apr. 5, 2012, which claims the benefit of priority from the prior Japanese Patent Application No. 2011-092027, filed on Apr. 18, 2011, the entire contents of which are incorporated herein by reference.

TECHNICAL FIELD

The present invention relates to a polymerizable compound, a polymerizable liquid crystal composition containing the compound, and an optically anisotropic body using the polymerizable composition.

BACKGROUND ART

Polymerizable compounds are used for various films. For example, films having uniform alignment can be formed by arranging polymerizable compounds in a liquid crystal state and polymerizing the compounds. The thus-formed films can be used for a polarizing plate, a retardation film, and the like necessary for liquid crystal displays. Also, polymerizable compounds can be used for forming films having a cholesteric structure. In many cases, compositions composed of two or more types of polymerizable compounds are used for satisfying required optical characteristics, polymerization rate, solubility, melting point, glass transition temperature, film transparency, mechanical strength, surface hardness, heat resistance, and light resistance. In this case, the polymerizable compounds used are required to impart good physical properties to the compositions without adversely affecting other characteristics. In particular, the purpose of forming a film having a cholesteric structure requires polymerizable compounds which can be present as a nematic phase or cholesteric phase within a wide temperature range and which have high nematic or cholesteric liquid crystal alignment properties. In addition, when a polymerizable liquid crystal composition is industrially used, high storage stability is required so as to avoid precipitation of polymerizable compounds in components even during long-term storage.

When the film having a cholesteric structure is used as a brightness enhancement film of a display or the like, the film is required to have a small haze value and a uniform cholesteric structure without unevenness. Therefore, polymerizable compounds having high alignment properties in addition to the above-described characteristics are desired. In addition, in order to adjust refractive index anisotropy of a composition to a desired value, not only a polymerizable compound having large refractive index anisotropy but also a polymerizable compound having small refractive index anisotropy is useful. However, generally known polymerizable compounds having small refractive index anisotropy have low storage stability and thus have the problem of precipitating crystals when a composition containing the polymerizable compounds is allowed to stand at room temperature for a long time. Also, due to low alignment properties, an optically anisotropic body produced by applying the composition on PET and drying the composition has the problem of increasing a haze value and causing unevenness (refer to Patent Literature 1 to Patent Literature 3). On the other hand, an example is reported, in which polymerizable compounds having a tolan skeleton introduced therein are used as liquid crystal materials having a high biaxial index, but any one of the polymerizable compounds has very large refractive index anisotropy, thereby increasing refractive index anisotropy of a composition (Patent Literature 4). Therefore, in order to adjust the refractive index anisotropy of a composition to a desired value, it is necessary to add a polymerizable compound having small refractive index anisotropy, but known polymerizable compounds having small refractive index anisotropy have the problem of unsatisfactory storage stability and alignment properties as described above.

CITATION LIST

Patent Literature

PTL 1: Japanese Unexamined Patent Application Publication No. 2008-195762
PTL 2: Japanese Unexamined Patent Application Publication No. 2008-88291
PTL 3: Publication No. GB2280445A
PTL 4: Publication No. EP1786887B1

SUMMARY OF INVENTION

Technical Problem

A problem to be solved by the invention is to provide a polymerizable compound having small refractive index anisotropy and having high storage stability and high alignment properties when constituting a polymerizable liquid crystal composition, and also provide a polymerizable liquid crystal composition containing the polymerizable compound. Further, the problem is to provide a polymer produced by polymerizing the polymerizable liquid crystal composition and an optically anisotropic body using the polymer.

Solution to Problem

As a result of study on various substituents of polymerizable compounds, the inventors of the present invention found that the problem can be resolved by a polymerizable compound having a specified structure, leading to the achievement of the present invention.

The present invention provides a polymerizable compound and a polymerizable liquid crystal composition using the compound, the polymerizable compound being represented by general formula (I),

[Chem. 1]

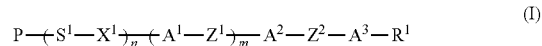

(in the formula, P represents a substituent selected from polymerizable groups represented by formulae (P-1) to (P-15) below,

[Chem. 2]

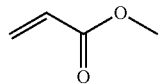
(P-1)

-continued

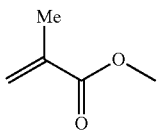 (P-2)

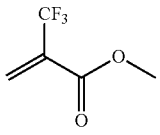 (P-3)

 (P-4)

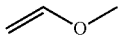 (P-5)

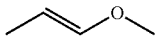 (P-6)

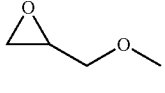 (P-7)

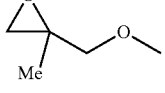 (P-8)

 (P-9)

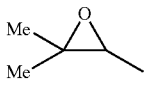 (P-10)

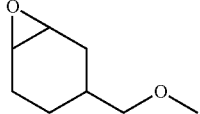 (P-11)

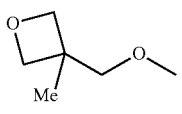 (P-12)

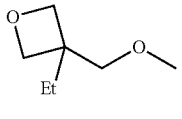 (P-13)

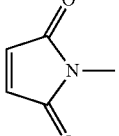 (P-14)

HS— (P-15)

$S^1$ represents an alkylene group having 1 to 20 carbon atoms, in which one —$CH_2$— or unadjacent two or more —$CH_2$— may be each independently substituted by —O—, or a single bond, and when a plurality of $S^1$ is present, $S^1$ may be the same or different; $X^1$ represents —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —$CH_2CH_2$—, —$CH_2CF_2$—, —$CF_2CH_2$—, —$CF_2CF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—OCO—, —$CH_2CH_2$—COO—, —$COOCH_2$—, —OCO—$CH_2$—, —$CH_2$—OCO—, —$CH_2$—COO—, —$CY^1$=$CY^2$—, —C≡C—, or a single bond (wherein $Y^1$ and $Y^2$ each independently represent a hydrogen atom, an alkyl group having 1 to 12 carbon atoms, a fluorine atom, a chlorine atom, or a CN group), and when a plurality of $X^1$ is present, $X^1$ may be the same or different; n represents 0, 1, 2, 3, or 4; $A^1$ and $A^2$ each independently represent a 1,4-phenylene group, a naphthalene-2,6-diyl group, a 1,4-cyclohexylene group, a 1,4-cyclohexenylene group, a 1,4-bicyclo[2.2.2]octylene group, a decahydronaphthalene-2,6-diyl group, a 1,2,3,4-tetrahydronaphthalene-2,6-diyl group, a pyridine-2,6-diyl group, a pyrimidine-2,5-diyl group, or a 1,3-dioxane-2,5-diyl group, which may be unsubstituted or substituted by a fluorine atom, a chlorine atom, a cyano group, a nitro group, an alkyl group having 1 to 7 carbon atoms, an alkoxy group having 1 to 7 carbon atoms, or an alkanoyl group having 1 to 7 carbon atoms; at least one hydrogen atom of the alkyl group, the alkoxy group, or the alkanoyl group may be substituted by a fluorine atom or chlorine atom, and when a plurality of $A^1$ is present, $A^1$ may be the same or different; $A^3$ represents a group selected from groups represented by formula ($A^3$-1) to formula ($A^3$-8) below,

[Chem. 3]

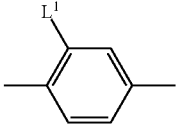 ($A^3$-1)

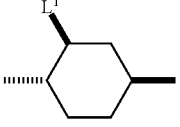 ($A^3$-2)

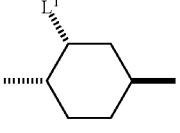 ($A^3$-3)

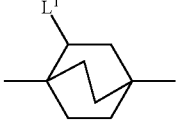 ($A^3$-4)

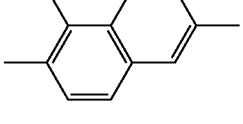 ($A^3$-5)

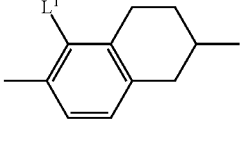 ($A^3$-6)

-continued

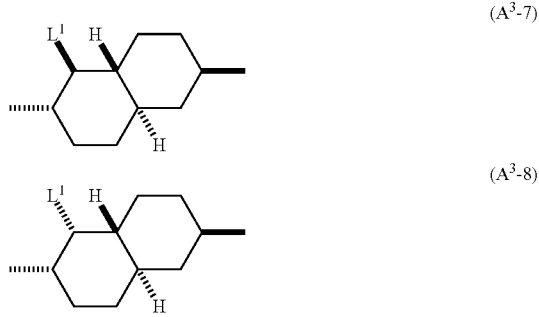

(in the formulae, $L^1$ represents an alkyl group, alkoxy group, or alkanoyl group having 1 to 7 carbon atoms, in which at least one hydrogen atom may be substituted by a fluorine atom or a chlorine atom), one —CH= or unadjacent two —CH= in a group represented by the formula ($A^3$-1) may be substituted by —N—, one —$CH_2$— or unadjacent two —$CH_2$— in groups represented by the formula ($A^3$-2) and formula ($A^3$-3) may be substituted by —O— or —S—, groups represented by the formula ($A^3$-1) to the formula ($A^3$-8) may be further substituted by a fluorine atom, a chlorine atom, a cyano group, a nitro group, an alkyl group having 1 to 7 carbon atoms, an alkoxy group having 1 to 7 carbon atoms, or an alkanoyl group having 1 to 7 carbon atoms, and at least one hydrogen atom of the alkyl group, the alkoxy group, or the alkanoyl group may be substituted by a fluorine atom or chlorine atom; $Z^1$ and $Z^2$ each independently represent —$OCH_2$—, —$CH_2O$—, —COO—, —OCO—, —CO—S—, —S—CO—, —CO—NH—, —NH—CO—, —$SCH_2$—, —$CH_2S$—, —$CF_2O$—, —$OCF_2$—, —$CF_2S$—, —$SCF_2$—, —$CH_2CH_2$—, —$CH_2CF_2$—, —$CF_2CH_2$—, —$CF_2CF_2$—, —CH=CH—COO—, —CH=CHOCO—, —COO—CH=CH—, —OCO—CH=CH—, —COO—$CH_2CH_2$—, —OCO—$CH_2CH_2$—, —$CH_2CH_2$—OCO—, —$CH_2CH_2$—COO—, —COO—$CH_2$—, —OCO—$CH_2$—, —$CH_2$—OCO—, —$CH_2$—COO—, —$CY^3$=$CY^4$—, or a single bond (wherein $Y^3$ and $Y^4$ each independently represents a hydrogen atom, an alkyl group having 1 to 12 carbon atoms, a fluorine atom, a chlorine atom, or a CN group), and when a plurality of $Z^1$ is present, $Z^1$ may be the same or different; $R^1$ represents a fluorine atom, a chlorine atom, a CN group, or an alkyl group having 1 to 12 carbon atoms, at least one hydrogen atom in the alkyl group may be substituted by a fluorine atom, a chlorine atom, or a cyano group, and one —$CH_2$— or unadjacent two or more —$CH_2$— in the alkyl group may be each independently substituted by —O—, —S—, —CO—, —COO—, —OCO—, —CO—S—, —S—CO—, —O—CO—O—, —CO—NH—, —NH—CO—, —CH=CH—, —CH=CF—, —CF=CH—, or —C≡C—; and m represents 0, 1, 2, 3, or 4).

Advantageous Effects of Invention

The polymerizable compound of the present invention has small refractive index anisotropy and exhibits high storage stability when constituting a polymerizable liquid crystal composition, and is thus useful as a constituent component of a polymerizable composition. Also, an optically anisotropic body using a composition containing the polymerizable compound of the present invention has high alignment properties and is thus useful for applications to an optical film and the like.

DESCRIPTION OF EMBODIMENTS

In general formula (I), P represents a polymerizable group represented by formula (P-1) to formula (P-15), and the polymerizable group is cured by radical polymerization, radical addition polymerization, cationic polymerization, or anionic polymerization. In particular, when ultraviolet polymerization is used as a polymerization method, the formula (P-1), the formula (P-2), the formula (P-3), the formula (P-4), the formula (P-5), the formula (P-7), the formula (P-11), the formula (P-13), or the formula (P-15) is preferred, the formula (P-1), the formula (P-2), the formula (P-7), the formula (P-11), or the formula (P-13) is more preferred, and the formula (P-1) or the formula (P-2) is particularly preferred.

$S^1$ represents an alkylene group having 1 to 20 carbon atoms, in which one —$CH_2$— or unadjacent two or more —$CH_2$— may be each independently substituted by —O—, or a single bond, but an alkylene group having 1 to 8 carbon atoms is preferred in view of liquid crystallinity and compatibility with other components.

$X^1$ represents —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —$CH_2CH_2$—, —$CH_2CF_2$—, —$CF_2CH_2$—, —$CF_2CF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—OCO—, —$CH_2CH_2$—COO—, —$CY^1$=$CY^2$—, —C≡C—, or a single bond (wherein $Y^1$ and $Y^2$ each independently represents a hydrogen atom, an alkyl group having 1 to 12 carbon atoms, a fluorine atom, a chlorine atom, or a CN group), —O—, —COO—, —OCO—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—OCO—, —$CH_2CH_2$—COO—, —COO—$CH_2$—, —OCO—$CH_2$—, —$CH_2$—OCO—, —$CH_2$—COO—, or a single bond is preferred, and —O— is particularly preferred.

n represents 0, 1, 2, 3, or 4, but 1 or 2 is preferred, and 1 is particularly preferred.

$A^1$ and $A^2$ each independently represent a 1,4-phenylene group, a naphthalene-2,6-diyl group, a 1,4-cyclohexylene group, a 1,4-cyclohexenylene group, a 1,4-bicyclo[2.2.2]octylene group, a decahydronaphthalene-2,6-diyl group, a 1,2,3,4-tetrahydronaphthalene-2,6-diyl group, a pyridine-2,6-diyl group, a pyrimidine-2,5-diyl group, or a 1,3-dioxane-2,5-diyl group, which may be unsubstituted or substituted by a fluorine atom, a chlorine atom, a cyano group, a nitro group, an alkyl group having 1 to 7 carbon atoms, an alkoxy group having 1 to 7 carbon atoms, or an alkanoyl group having 1 to 7 carbon atoms, at least one hydrogen atom of the alkyl group, the alkoxy group, or the alkanoyl group may be substituted by a fluorine atom or chlorine atom, and when a plurality of $A^1$ is present, $A^1$ may be the same or different. However, a 1,4-phenylene group which is unsubstituted or substituted by a fluorine atom, a chlorine atom, an alkyl group having 1 to 4 carbon atoms, or an alkoxy group having 1 to 4 carbon atoms, a naphthalene-2,6-diyl group which is unsubstituted or substituted by a fluorine atom or a chlorine atom, or an unsubstituted 1,4-cyclohexenylene group, in which one —$CH_2$— or unadjacent two —$CH_2$— may be substituted by —O—, is preferred, and a 1,4-phenylene group which is unsubstituted or substituted by a fluorine atom, a chlorine atom, a $CH_3$ group, a $CH_3O$ group, an unsubstituted naphthalene-2,6-diyl group, or an unsubstituted 1,4-cyclohexenylene group is particularly preferred.

$A^3$ represents a group selected from groups represented by formula ($A^3$-1) to formula ($A^3$-8) below,

[Chem. 4]

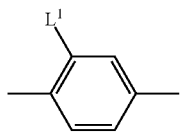
($A^3$-1)

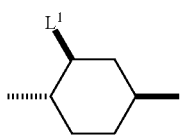
($A^3$-2)

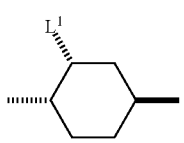
($A^3$-3)

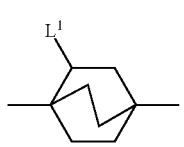
($A^3$-4)

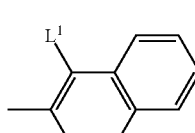
($A^3$-5)

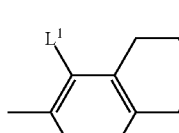
($A^3$-6)

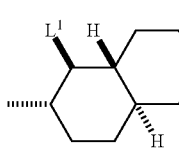
($A^3$-7)

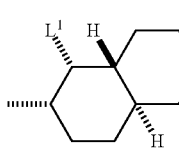
($A^3$-8)

(in the formulae, $L^1$ represents an alkyl group, alkoxy group, or alkanoyl group having 1 to 7 carbon atoms, in which at least one hydrogen atom may be substituted by a fluorine atom or a chlorine atom), one —CH═ or unadjacent two —CH═ in a group represented by the formula ($A^3$-1) may be substituted by —N═, one —CH$_2$— or unadjacent two —CH$_2$— in groups represented by the formula ($A^3$-2) and formula ($A^3$-3) may be substituted by —O— or —S—, groups represented by the formula ($A^3$-1) to the formula ($A^3$-8) may be further substituted by a fluorine atom, a chlorine atom, a cyano group, a nitro group, an alkyl group having 1 to 7 carbon atoms, an alkoxy group having 1 to 7 carbon atoms, or an alkanoyl group having 1 to 7 carbon atoms, and at least one hydrogen atom of the alkyl group, the alkoxy group, or the alkanoyl group may be substituted by a fluorine atom or chlorine atom. However, a group represented by the formula ($A^3$-1) or the formula ($A^3$-5) is preferred, in which $L^1$ represents an alkyl group or alkoxy group having 1 to 4 carbon atoms, and a hydrogen atom on a benzene ring or a naphthalene ring may be substituted by a fluorine atom, a chlorine atom, or an alkyl group or alkoxy group having 1 to 4 carbon atoms, and a group represented by the formula ($A^3$-1) or the formula ($A^3$-5) is particularly preferred, in which $L^1$ represents a CH$_3$ group or CH$_3$O group, and a hydrogen atom on a benzene ring or a naphthalene ring may be substituted by a fluorine atom, a chlorine atom, or a CH$_3$ group or CH$_3$O group.

$Z^1$ and $Z^2$ each independently represent —OCH$_2$—, —CH$_2$O—, —COO—, —OCO—, —CO—S—, —S—CO—, —CO—NH—, —NH—CO—, —SCH$_2$—, —CH$_2$S—, —CF$_2$O—, —OCF$_2$—, —CF$_2$S—, —SCF$_2$—, CH$_2$CH$_2$—, —CH$_2$CF$_2$—, —CF$_2$CH$_2$—, —CF$_2$CF$_2$—, —CH═CH—COO—, —CH═CHOCO—, —COO—CH═CH—, —OCO—CH═CH—, —COO—CH$_2$CH$_2$—, —OCO—CH$_2$CH$_2$—, —CH$_2$CH$_2$—OCO—, —CH$_2$CH$_2$—COO—, —COO—CH$_2$—, —OCO—CH$_2$—, —CH$_2$—OCO—, —CH$_2$—COO—, —CY$^3$═CY$^4$—, or a single bond (wherein $Y^3$ and $Y^4$ each independently represent a hydrogen atom, an alkyl group having 1 to 12 carbon atoms, a fluorine atom, a chlorine atom, or a cyano group), and when a plurality of $Z^1$ is present, $Z^1$ may be the same or different. However, —COO—, —OCO—, —CH═CH—COO—, —CH═CHOCO—, —COO—CH═CH—, —OCO—CH═CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, CH$_2$—OCO—, or a single bond is preferred, and —COO—, —OCO—, —CH═CH—COO—, —COO—CH═CH—, or a single bond is particularly preferred.

$R^1$ represents a fluorine atom, a chlorine atom, a cyano group, or an alkyl group having 1 to 12 carbon atoms, at least one hydrogen atom present in the alkyl group may be substituted by a fluorine atom, a chlorine atom, or a cyano group, and one —CH$_2$— or unadjacent two or more —CH$_2$— in the alkyl group may be each independently substituted by —O—, —S—, —CO—, —COO—, —OCO—, —CO—S—, —S—CO—, —O—CO—O—, —CO—NH—, —NH—CO—, —CH═CH—, —CH═CF—, —CF═CH—, or —C≡C—. However, an alkyl group having 1 to 8 carbon atoms is particularly preferred, and more preferably linear.

m represents 0, 1, 2, 3, or 4, but 1, 2, or 3 is preferred, and 1 or 2 is particularly preferred.

Preferred examples of the compound represented by the general formula (I) include compounds represented by formula (I-1) to formula (I-15) below.

[Chem. 5]
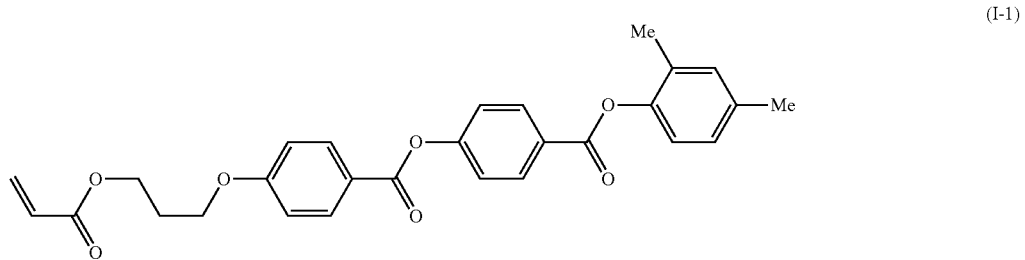 (I-1)
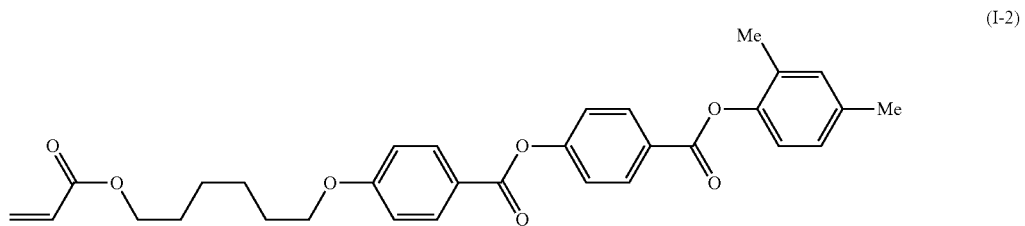 (I-2)
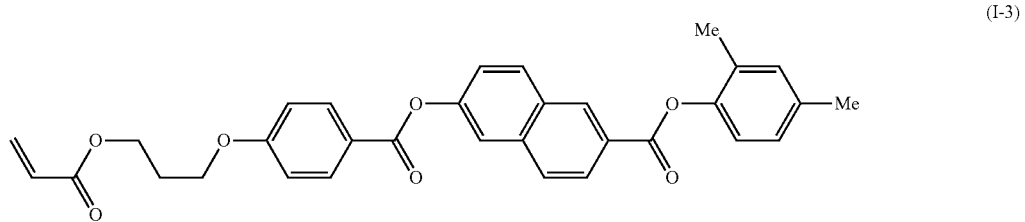 (I-3)
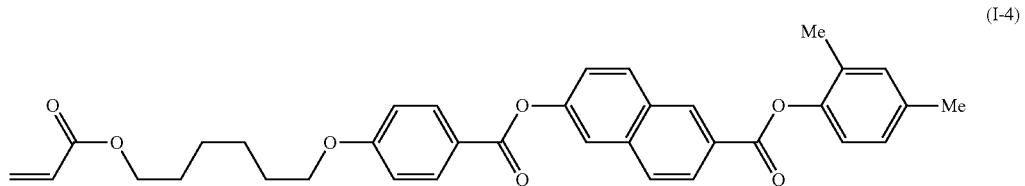 (I-4)
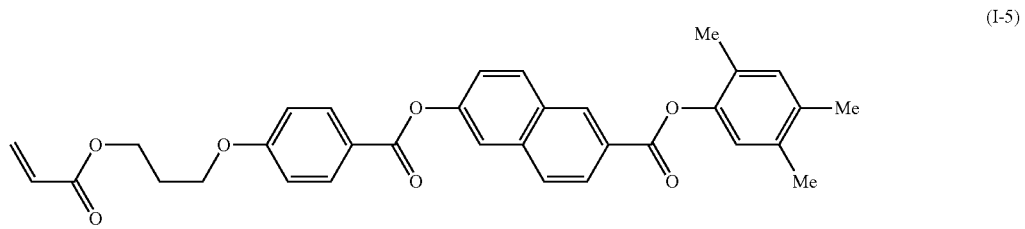 (I-5)
[Chem. 6]
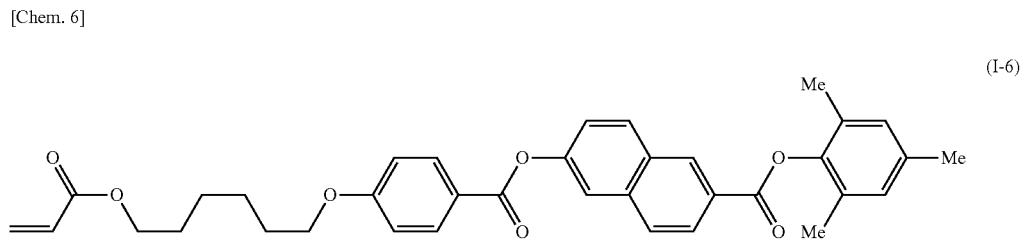 (I-6)
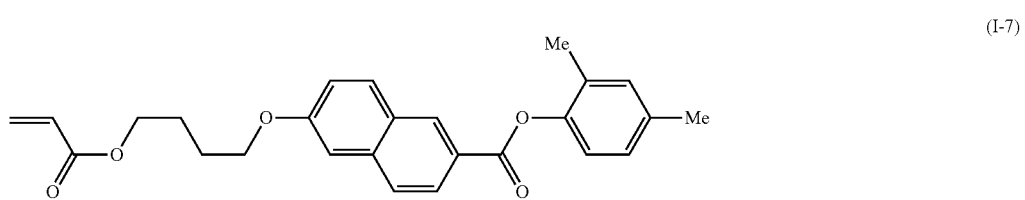 (I-7)

(I-8)
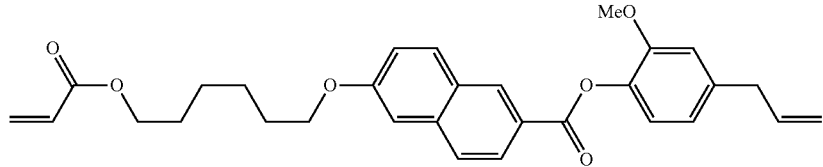
(I-9)
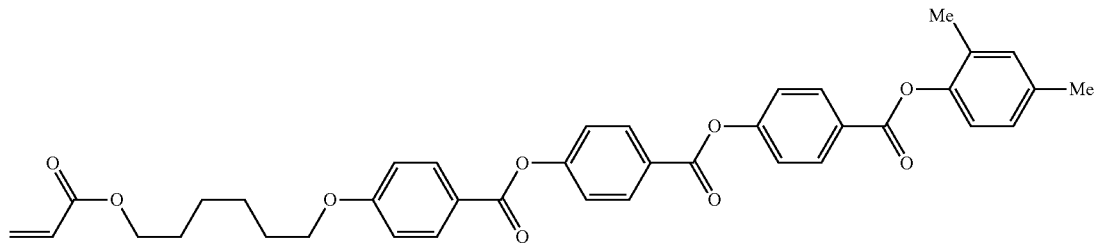
(I-10)
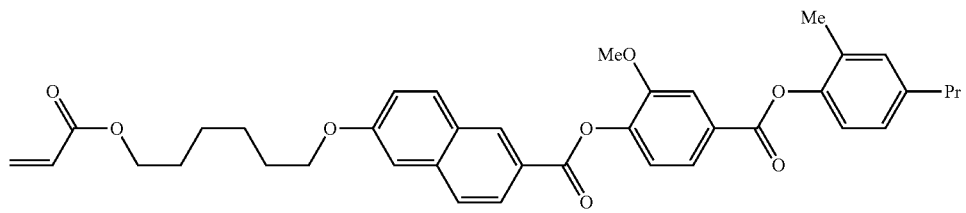
[Chem. 7]
(I-11)
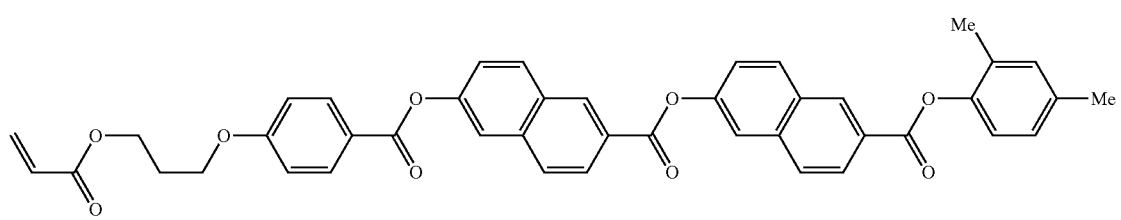
(I-12)
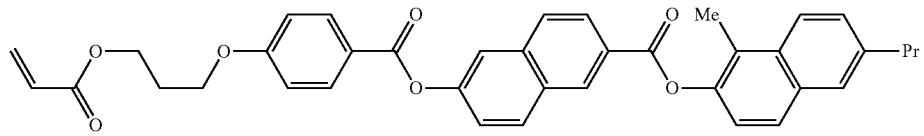
(I-13)
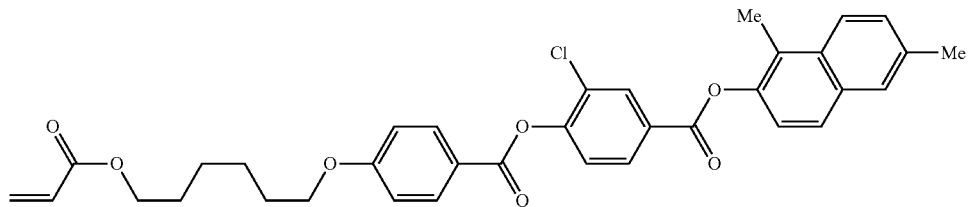
(I-14)
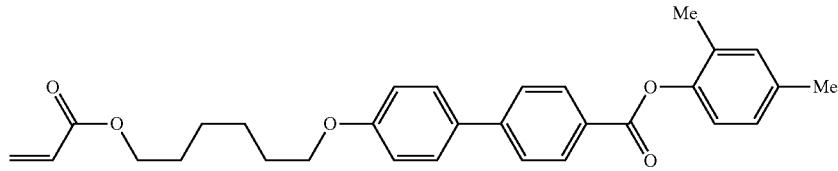

-continued

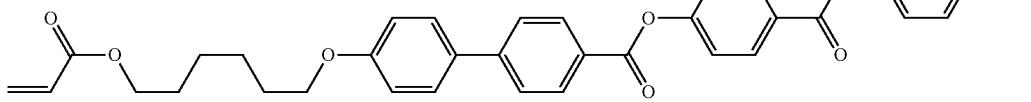
(I-15)

Compounds of the present invention can be produced by production methods below.

(Method 1) Production of Compound (S6) Below

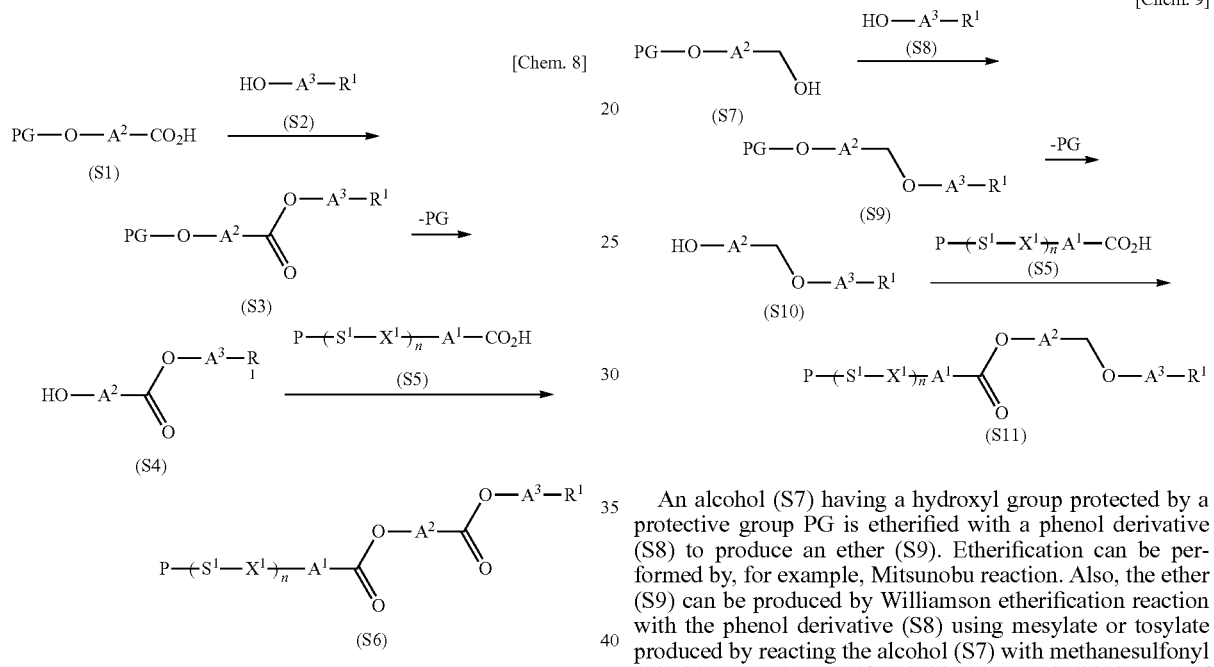

A carboxylic acid (S1) having a hydroxyl group protected by a protective group PG is condensed with a phenol derivative (S2) to produce an ester (S3). The protective group (PG) is not particularly limited as long as it can stably protect a functional group in a synthesis process and can be easily removed, and, for example, protective groups described in GREENE'S PROTECTIVE GROUPS IN ORGANIC SYNTHESIS (Fourth Edition), by PETER G. M. WUTS and THEODORA W. GREENE, A John Wiley & Sons, Inc., Publication can be used. Condensation can be performed by using an acid catalyst such as sulfuric acid, hydrochloric acid, nitric acid, acetic acid, formic acid, trifluoroacetic acid, p-toluenesulfonic acid, or the like, or a carbodiimide condensing agent such as N,N'-dicyclohexyl-carbodiimide, N,N'-diisopropylcarbodiimide, 1-ethyl-3-(3-dimethylaminopropyl) carbodiimide hydrochloride, or the like. Also, a method through Mitsunobu reaction or carboxylic acid halide can be used. Then, an intermediate (S4) produced by removing the protective group PG according to a method described in the above document is condensed with a carboxylic acid (S5) to produce the target product (S6).

(Method 2) Production of Compound (S11) Below

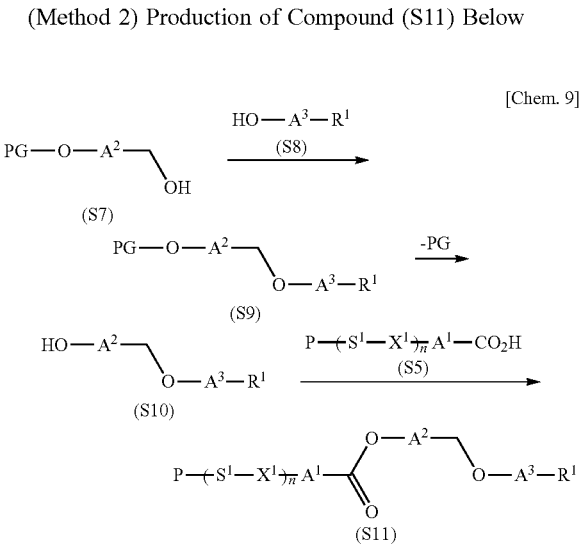

An alcohol (S7) having a hydroxyl group protected by a protective group PG is etherified with a phenol derivative (S8) to produce an ether (S9). Etherification can be performed by, for example, Mitsunobu reaction. Also, the ether (S9) can be produced by Williamson etherification reaction with the phenol derivative (S8) using mesylate or tosylate produced by reacting the alcohol (S7) with methanesulfonyl chloride or p-toluenesulfonyl chloride, or a halide instead of the alcohol (S7). Then, an intermediate (S10) produced by removing the protective group PG is condensed with a carboxylic acid (S5) to produce the target product (S11).

(Method 3) Production of Compound (S16) Below

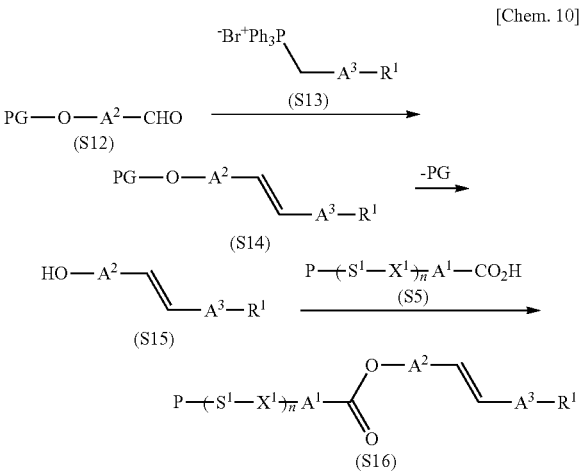

An aldehyde (S12) having a hydroxyl group protected by a protective group (PG) is reacted with a phosphonium salt (S13) in the presence of a base to produce an ethene intermediate (S14). Then, an intermediate (S15) produced by removing the protective group PG is condensed with a carboxylic acid (S5) to produce the target product (S16).

(Method 4) Production of Compound (S18) Below

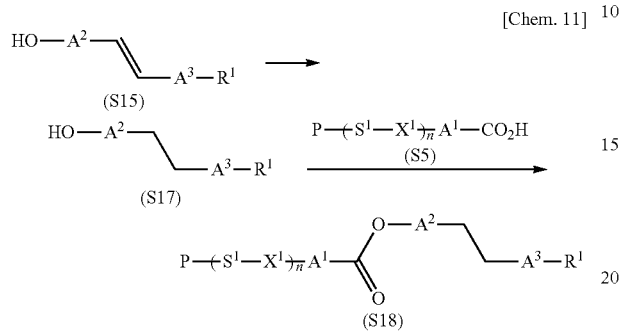

The ethene intermediate (S15) is reduced by hydrogenation to produce an ethylene intermediate (S17). Then, the intermediate (S17) is condensed with a carboxylic acid (S5) to produce the target product (S18).

(Method 5) Production of Compound (S24) Below

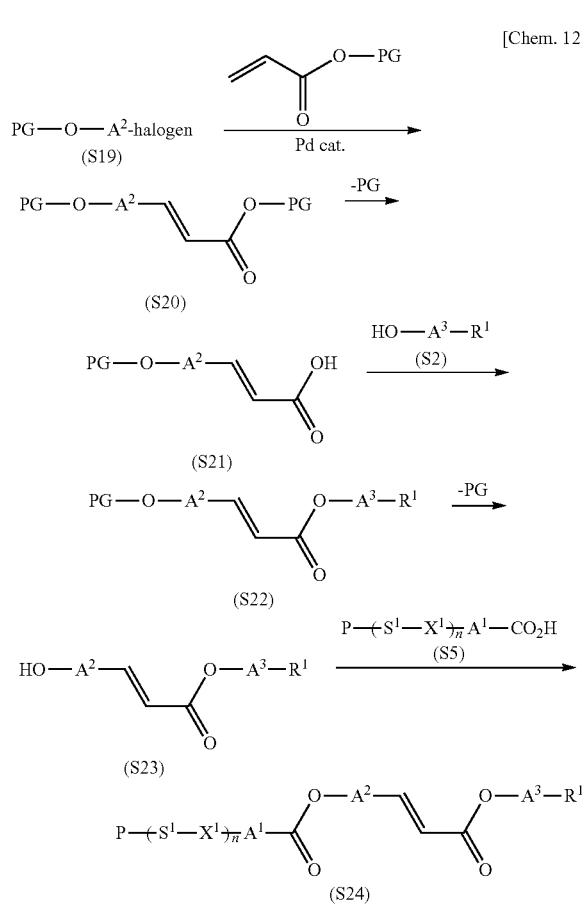

A halide (S19) having a hydroxyl group protected by a protective group PG is reacted with a protected acrylate in the presence of a palladium catalyst to produce an ester intermediate (S20). Then, a carboxylic acid intermediate (S21) produced by removing only the protective group PG on the ester side is condensed with a phenol derivative (S2) to produce an ester intermediate (S22). An intermediate (S23) produced by removing the protective group PG is condensed with a carboxylic acid (S5) to produce the target product (S24).

(Method 6) Production of Compound (S29) Below

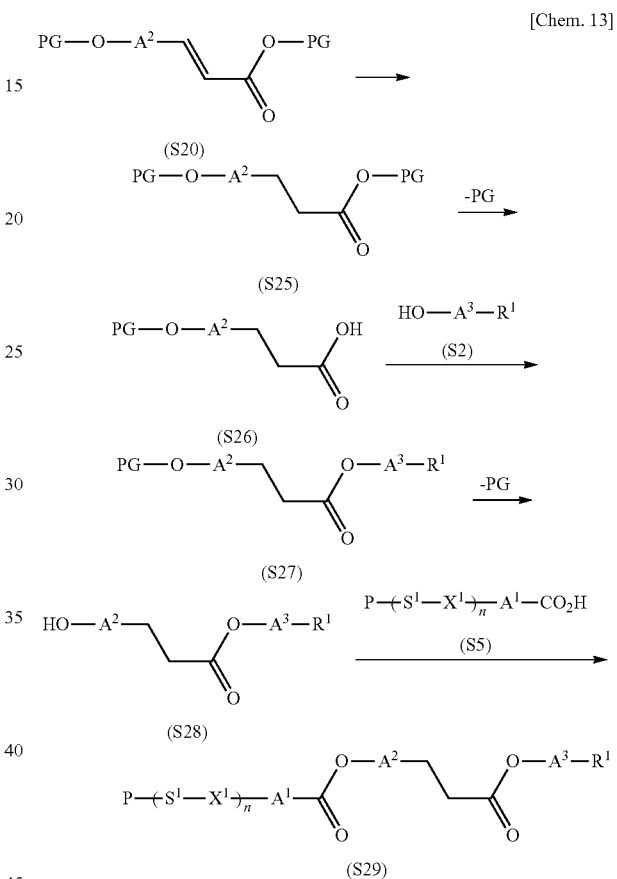

The ester intermediate (S20) is reduced by hydrogenation to produce an ester intermediate (S25). Then, a carboxylic acid intermediate (S26) produced by removing only the protective group PG on the ester side is condensed with a phenol derivative (S2) to produce an ester intermediate (S27). An intermediate (S28) produced by removing the protective group PG is condensed with a carboxylic acid (S5) to produce a target product (S29).

The compound of the present invention is preferably used for a nematic liquid crystal composition, a smectic liquid crystal composition, a chiral smectic liquid crystal composition, and a cholesteric liquid crystal composition, and particularly preferably used for a cholesteric liquid crystal composition. A compound other than the compound of the present invention may be added to a liquid crystal composition using the polymerizable compound of the present invention.

Specifically, the other polymerizable compound used to be mixed with the polymerizable compound of the present invention is preferably represented by general formula (II),

[Chem. 14]

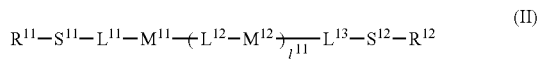

(II)

(in the formula, $R^{11}$ and $R^{12}$ each independently represent the same meaning as P in the general formula (I), $S^{11}$ and $S^{12}$ each independently represent a single bond or an alkylene group having 1 to 18 carbon atoms, wherein one —$CH_2$— or unadjacent two or more —$CH_2$— may be substituted by an oxygen atom, —COO—, —OCO—, or —OCOO—, $L^{11}$, $L^{12}$, and $L^{13}$ each independently represent a single bond, —O—, —S—, —$OCH_2$—, —$CH_2O$—, —CO—, —COO—, —OCO—, —CO—S—, —S—CO—, —O—CO—O—, —$OCOOCH_2$—, —$CH_2OCO$—, —CO—$NR^{13}$—, —$NR^{13}$—CO—, —$SCH_2$—, —$CH_2S$—, —CH=N—, —$SCH_2$—, —$CH_2S$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —$CF_2$—, —$CF_2O$—, —$OCF_2$—, —$CH_2CH_2$—, —$CF_2CH_2$—, —$CH_2CF_2$—, —$CF_2CF_2$—, —$CY^{11}$=$CY^{12}$—, or —C≡C—(wherein $R^{13}$ represents an alkyl group having 1 to 4 carbon atoms, and $Y^{11}$ and $Y^{12}$ each independently represent a hydrogen atom, an alkyl group having 1 to 12 carbon atoms, a fluorine atom, a chlorine atom, or a cyano group), $M^{11}$ and $M^{12}$ each independently represent a 1,4-phenylene group, a 1,4-cyclohexylene group, a pyridine-2,5-diyl group, a pyrimidine-2,5-diyl group, a naphthalene-2,6-diyl group, a tetrahydronaphthalene-2,6-diyl group, or a 1,3-dioxane-2,5-diyl group, $M^{11}$ and $M^{12}$ may be each independently unsubstituted or substituted by an alkyl group, a halogenated alkyl group, an alkoxy group, a halogenated alkoxy group, a halogeno group, a cyano group, or a nitro group, $l^{11}$ represents 0, 1, 2, or 3, when $l^{11}$ represents 2 or 3, two or three $L^{12}$ and/or $M^{12}$ may be the same or different, $L^{11}$, $L^{12}$, and $L^{13}$ each independently represent a single bond, —O—, —COO—, or —OCO—, and $M^{11}$ and $M^{12}$ each independently represent a 1,4-phenylene group, a 1,4-cyclohexylene group, a pyridine-2,5-diyl group, a pyrimidine-2,5-diyl group, or a naphthalene-2,6-diyl group).

Further, $R^{11}$ and $R^{12}$ in the general formula (II) are preferably acryl groups or methacryl groups. Specifically, compounds represented by general formula (III) are preferred,

[Chem. 15]

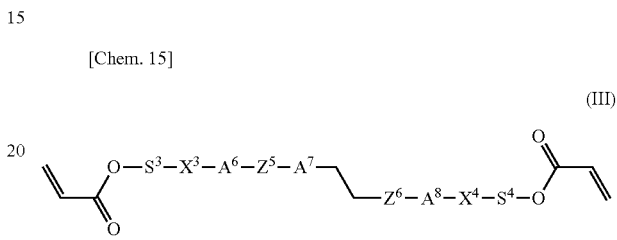

(III)

(in the formula, $S^3$ and $S^4$ each independently represent an alkylene group having 2 to 18 carbon atoms, $X^3$ and $X^4$ each independently represent —O—, —COO—, —OCO—, or a single bond, $Z^5$ and $Z^6$ each independently represent —COO— or —OCO—, and $A^6$, $A^7$, and $A^8$ each independently represent a 1,4-phenylene group which is unsubstituted or substituted by a fluorine atom, a chlorine atom, an alkyl group having 1 to 4 carbon atoms, or an alkoxy group having 1 to 4 carbon atoms), compounds represented by formula (III-1) to formula (III-8) below are particularly preferred,

[Chem. 16]

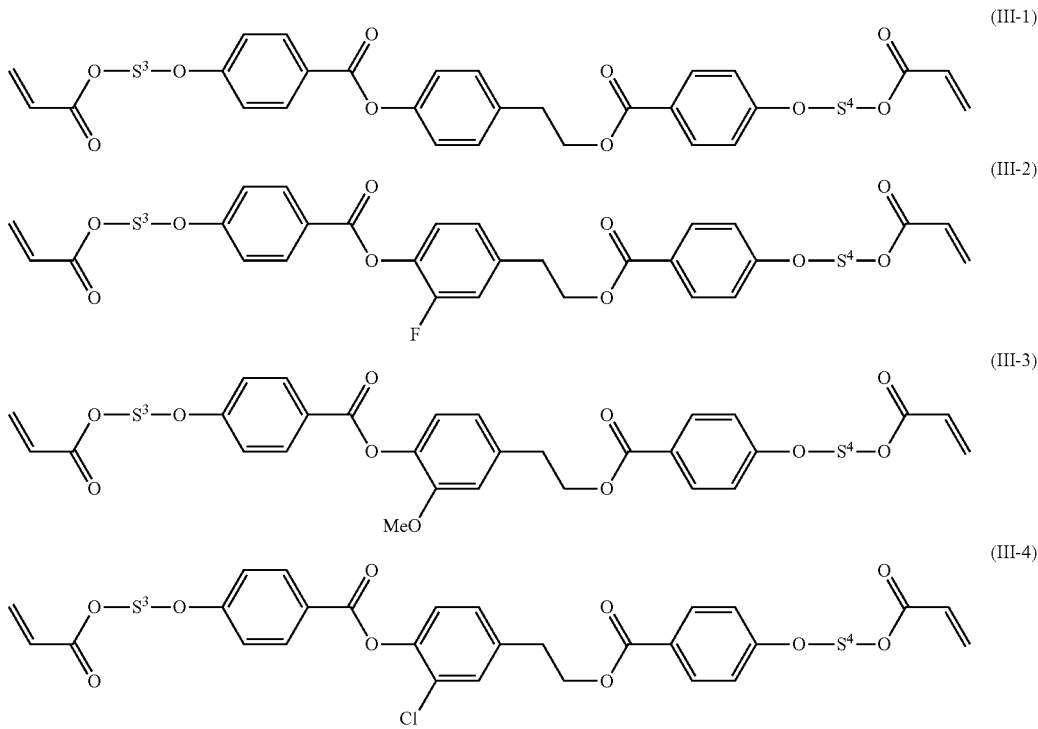

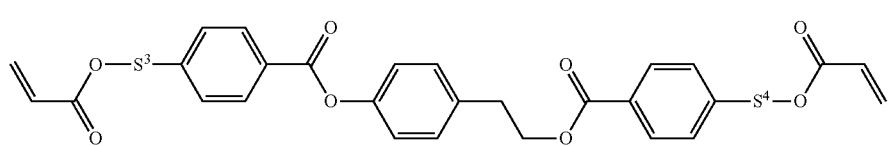
(III-5)

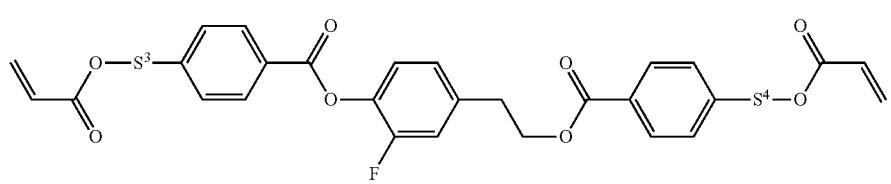
(III-6)

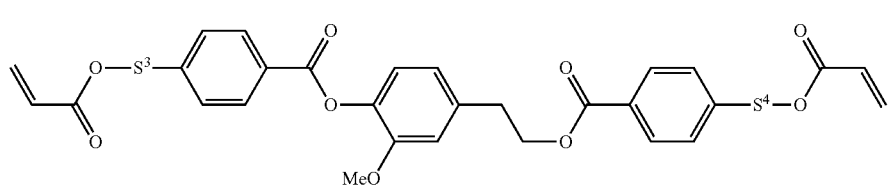
(III-7)

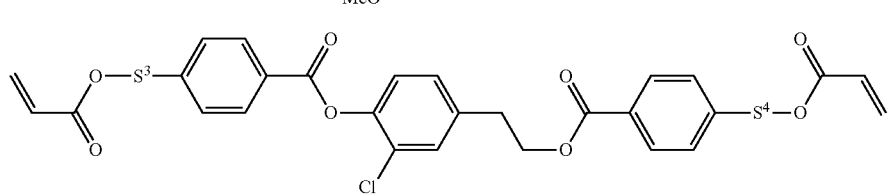
(III-8)

(in the formulae, $S^3$ represent the same meaning as $S^3$ in the general formula (III), and $S^4$ represent the same meaning as $S^4$ in the general formula (III)), and compounds in which $S^3$ and $S^4$ in the formula (III-1) to the formula (III-8) each independently represent an alkylene group having 3 to 6 carbon atoms are more preferred.

Also, compounds represented by general formula (IV) are preferred,

[Chem. 17]

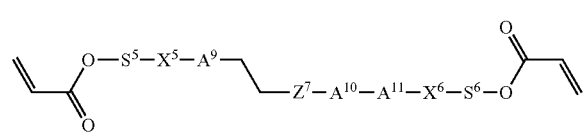
(IV)

(in the formula, $S^5$ and $S^6$ each independently represent an alkylene group having 2 to 18 carbon atoms, $X^5$ and $X^6$ each independently represent —O—, —COO—, —OCO—, or a single bond, $Z^7$ represents —COO— or —OCO—, and $A^9$, $A^{10}$, and $A^{11}$ each independently represent a 1,4-phenylene group which is unsubstituted or substituted by a fluorine atom, a chlorine atom, an alkyl group having 1 to 4 carbon atoms, or an alkoxy group having 1 to 4 carbon atoms), and compounds represented by formula (IV-1) to formula (IV-8) below are particularly preferred,

[Chem. 18]

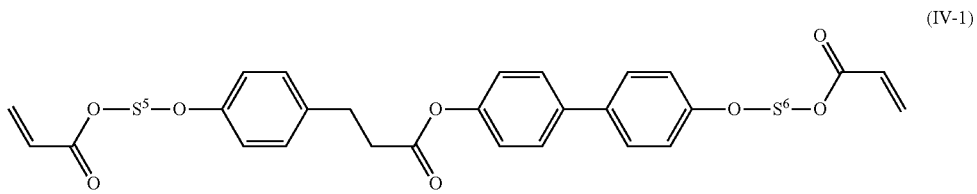
(IV-1)

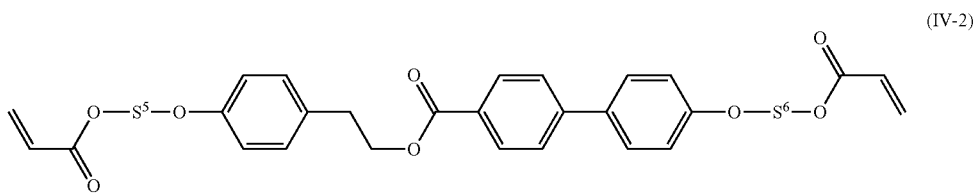
(IV-2)

-continued

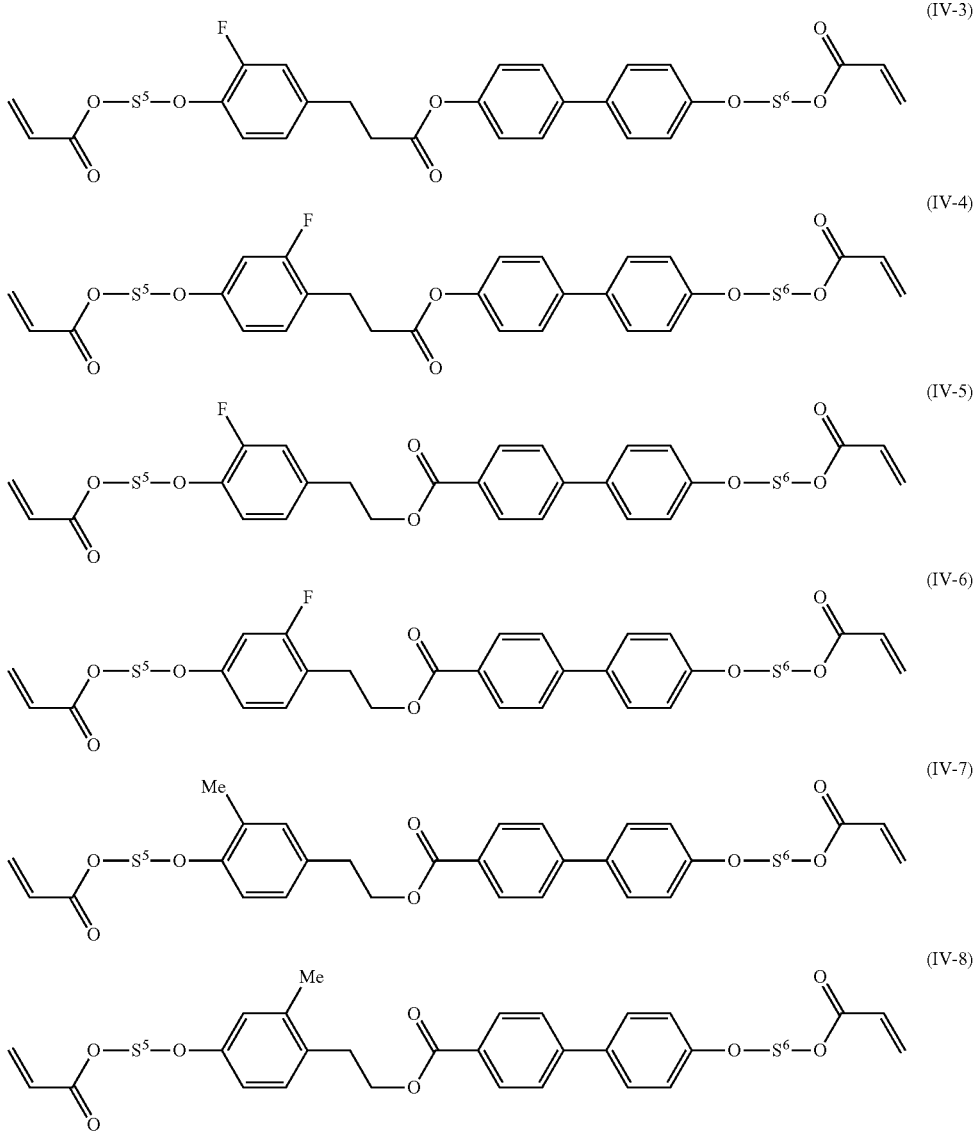

(in the formula, $S^5$ represents the same meaning as $S^5$ in the general formula (IV), and $S^6$ represents the same meaning as $S^6$ in the general formula (IV)). Among the formula (IV-1) to the formula (IV-8), compounds represented by the formula (IV-2), the formula (IV-5), the formula (IV-6), the formula (IV-7), and the formula (IV-8) are preferred in view of heat resistance and durability, a compound represented by the formula (IV-2) is more preferred, and a compound in which $S^5$ and $S^6$ are each independently an alkylene group having 3 to 6 carbon atoms is particularly preferred.

Other preferred difunctional polymerizable compounds include compounds represented by general formula (V-1) to formula (V-4) below,

[Chem. 19]

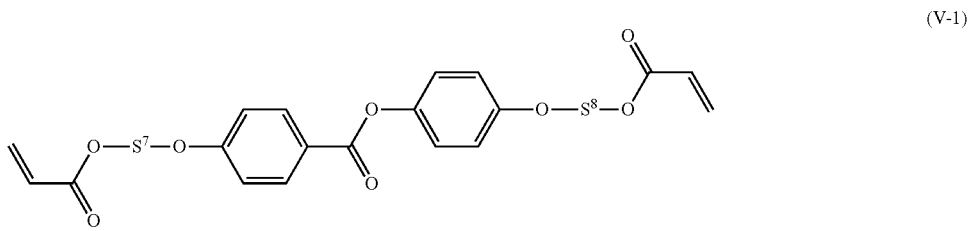

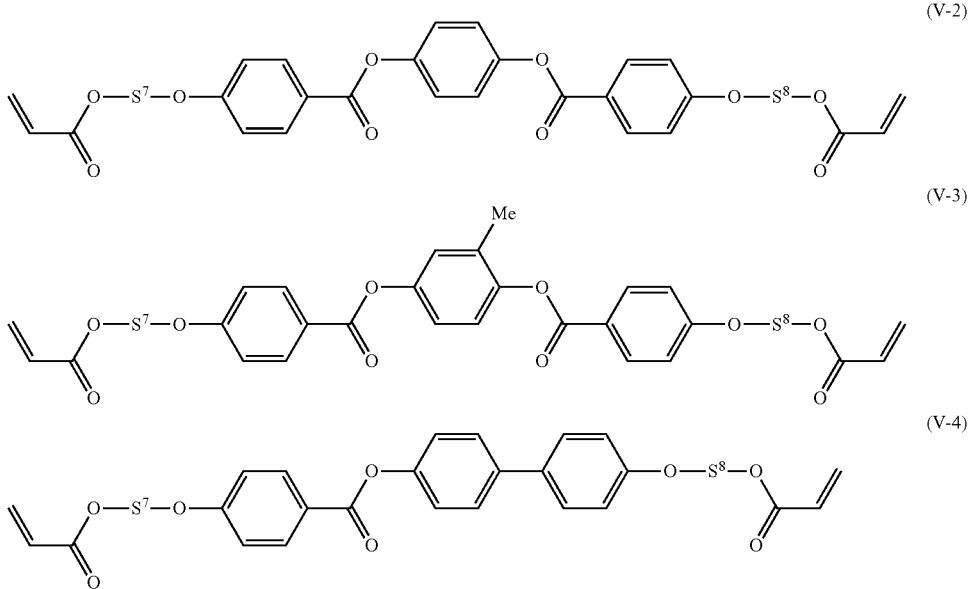

(in the formulae, $S^7$ and $S^8$ each independently represent an alkylene group having 2 to 18 carbon atoms). Among the formula (V-1) to the formula (V-4), compounds represented by the formula (V-2) and the formula (V-3) are preferred, and a compound in which $S^7$ and $S^8$ are each independently an alkylene group having 3 to 6 carbon atoms is particularly preferred.

When the compound of the present invention is used for a cholesteric liquid crystal composition, the amount of a polymerizable chiral compound added is preferably 0.1% to 40% by mass. Also, a polymerizable compound not exhibiting liquid crystallinity can be added to the polymerizable liquid crystal composition containing the compound of the present invention so as not to impair the liquid crystallinity of the composition. Specifically, any compound can be used without limitation as long as it is recognized as a polymer-forming monomer or a polymer-forming oligomer in this technical field.

The concentration of a photopolymerization initiator added to the polymerizable liquid crystal composition containing the compound of the present invention is preferably 0.1% to 10% by mass and more preferably 0.2% to 5% by mass. As the photopolymerization initiator, benzoinethers, benzophenones, acetophenones, benzylketals, acylphosphine oxide, and the like can be used.

Also, a stabilizer can be added to the polymerizable liquid crystal composition containing the compound of the present invention in order to improve storage stability of the composition. Examples of the stabilizer include hydroquinone, hydroquinone monoalkyl ethers, tert-butyl catechols, pyrogallols, thiophenols, nitro compounds, β-naphthylamines, β-naphthols, nitroso compounds, and the like. When the stabilizer is used, an adding amount is preferably 0.005% to 1% by mass and more preferably 0.02% to 0.5% by mass relative to the liquid crystal composition.

When the polymerizable liquid crystal composition containing the compound of the present invention is used for applications such as films, optical elements, functional pigments, medical products, cosmetics, coating agents, synthetic resins, and the like, a metal, a metal complex, a dye, a pigment, a colorant, a fluorescent material, a phosphorescent material, a surfactant, a leveling agent, a thixotropic agent, a gelling agent, a polysaccharide, an ultraviolet absorber, an infrared absorber, an antioxidant, an ion exchange resin, a metal oxide such as titanium oxide, and the like can be added according to purposes.

A polymer produced by polymerizing the polymerizable liquid crystal composition containing the compound of the present invention can be used for various applications. For example, a polymer produced by polymerizing, without alignment, the polymerizable liquid crystal composition containing the compound of the present invention can be used for a light scattering plate, a depolarization plate, or a Moire fringe preventing plate. A polymer produced by polymerization after alignment has optical anisotropy and is thus useful. Such an optically anisotropic body can be produced by supporting the polymerizable liquid crystal composition containing the compound of the present invention on a substrate rubbed with a cloth or the like, a substrate having an organic thin film, or a substrate having an alignment film formed by oblique deposition of $SiO_2$, or by holding the polymerizable liquid crystal composition between substrates, and then polymerizing the polymerizable liquid crystal composition.

Examples of a method for supporting the polymerizable liquid crystal composition on the substrate include spin coating, die coating, extrusion coating, roll coating, wire bar coating, gravure coating, spray coating, dipping, printing, and the like. Also, an organic solvent may be added to the polymerizable liquid crystal composition during coating. As the organic solvent, a hydrocarbon solvent, a halogenated hydrocarbon solvent, an ether solvent, an alcohol solvent, a ketone solvent, an ester solvent, an aprotic solvent, and the like can be used. Examples of the hydrocarbon solvent include toluene and hexane; examples of the halogenated hydrocarbon solvent include methylene chloride; examples of the ether solvent include tetrahydrofuran, acetoxy-2-ethoxyethane, and propylene glycol monomethyl ether acetate; examples of the alcohol solvent include methanol ethanol, and isopropanol; examples of the ketone solvent include acetone, methyl ethyl ketone, cyclohexanone, γ-butyrolactone, and N-methylpyrroridinone; examples of the ester solvent include ethyl acetate and cellosolve; and examples of the aprotic solvent include dimethylformamide and acetonitrile. These may be used alone or in combination, and the organic solvent may be appropriately selected in view of its vapor pressure and solubility of the polymerizable liquid crystal composition. As a method for evaporating the organic solvent added, air drying, drying by heating, reduced-pressure drying, and reduced-pressure drying by heating can be used. In order to further improve coatability of a polymerizable liquid crystal material, it is effective to provide an intermediate layer of a polyimide thin film or the like on a substrate or add a leveling agent to the polymerizable liquid crystal material. The method of providing an intermediate layer of a polyimide thin film or the like on a substrate is effective for improving adhesion between the substrate and a polymer produced by polymerizing the polymerizable liquid crystal material.

Examples of alignment other than the above include flow alignment of a liquid crystal material and electric-field or magnetic-field alignment. These alignment methods may be used alone or in combination. Further, a light alignment method can be used as an alignment method alternative to rubbing. The shape of the substrate may be a plate shape or a shape having a curved surface as a component. Either an organic material or an inorganic material can be used as a material constituting the substrate. Examples of the organic material used as the material of the substrate include polyethylene terephthalate, polycarbonate, polyimide, polyamide, polymethyl methacrylate, polystyrene, polyvinyl chloride, polytetrafluoroethylene, polychlorotrifluoroethylene, polyarylate, polysulfone, triacetyl cellulose, cellulose, polyether-ether ketone, and the like. Examples of the inorganic material include silicon, glass, calcite, and the like.

When the polymerizable liquid crystal composition containing the compound of the present invention is polymerized, polymerization preferably rapidly proceeds, and thus a preferred polymerization method includes irradiation with active energy rays such as ultraviolet light or electron beams. When ultraviolet light is used, either a polarized light source or an unpolarized light source may be used. When the liquid crystal composition held between two substrates is polymerized, at least the substrate on the irradiation surface side is required to have proper transparency to active energy rays. Also, another method may be used, in which only a specified portion is polymerized by irradiation using a mask, and then the alignment state of an unpolymerized portion is changed by changing a condition such as an electric field, a magnetic field, or temperature, followed by further polymerization by irradiation with active energy rays. The temperature during irradiation is preferably within a temperature range in which the liquid crystal state of the polymerizable liquid crystal composition of the present invention is maintained. In particular, when an optically anisotropic body is produced by photopolymerization, polymerization is preferably performed at a temperature as close to room temperature as possible, that is, typically a temperature of 25° C., in order to avoid induction of unintended heat polymerization. The intensity of active energy rays is preferably 0.1 mW/cm$^2$ to 2 W/cm$^2$. With an intensity of 0.1 mW/cm$^2$ or less, much time is required for completing photopolymerization, thereby degrading productivity, while an intensity of 2 W/cm$^2$ or more, the polymerizable liquid crystal compound or polymerizable liquid crystal composition may be degraded.

Also the optically anisotropic body produced by polymerization can be heat-treated for the purpose of decreasing a change in initial characteristics and exhibiting stabile characteristics. A heat treatment temperature is preferably within a range of 50° C. to 250° C., and a heat treatment time is preferably within a range of 30 seconds to 12 hours.

The optically anisotropic body produced by the above-described method may be separated from the substrate and used as a single body or may be used without being separated. Also, the resultant optically anisotropic body may be used in lamination or by being bonded to another substrate.

EXAMPLES

The present invention is described in further detail below by way of examples, but the present invention is not limited to these examples. In the examples and comparative examples, "%" in a composition represents "% by mass".

(Example 1) Production of Compound Represented by Formula (I-1)

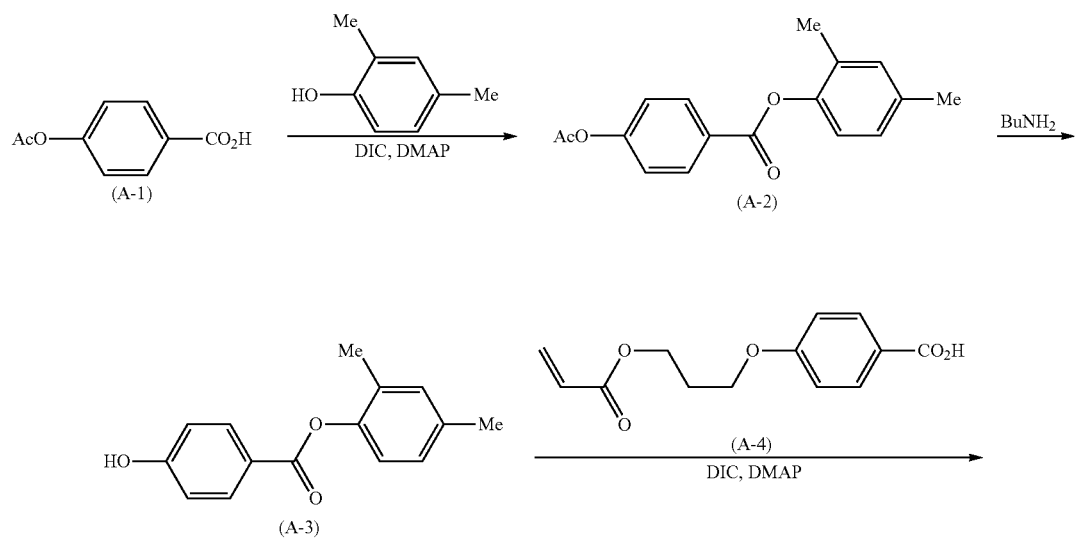

[Chem. 20]

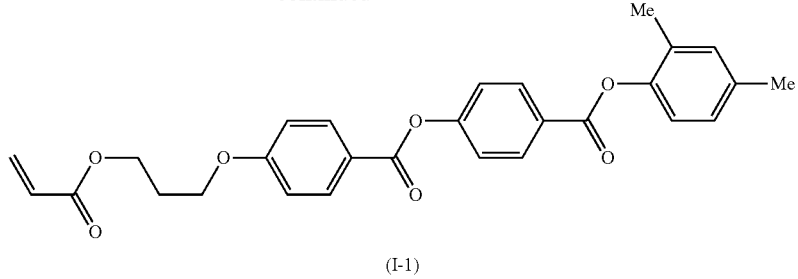

(I-1)

In a reactor provided with a stirrer and a thermometer, 20.0 g (0.11 mole) of 4-acetoxybenzoic acid (compound represented by formula (A-1)), 12.3 g (0.10 mole) of 2,4-dimethylphenol, 0.6 g (5.0 millimole) of N,N-dimethylaminopyridine (DMAP), and 100 mL of dichloromethane were added and stirred under ice cooling. Then, 15.3 g (0.12 mole) of N,N'-diisopropylcarbodiimide (DIC) was added dropwise while the temperature of the reaction solution was kept at 15° C. or less. After the completion of addition, reaction was performed by stirring at room temperature for 5 hours. The reaction solution was filtered to remove precipitates, and then the solvent was distilled off. The resultant solid was dissolved in dichloromethane and purified by column chromatography (purifying agent: silica gel 29 g, eluent: dichloromethane 232 mL), and then the solvent was distilled off. The resultant solid was dispersed and washed with 87 mL of methanol and then dried to produce 26.7 g of a compound represented by formula (A-2).

In a reactor provided with a stirrer and a thermometer, 26.7 g (0.094 mole) of the compound represented by the formula (A-2), 80 mL of toluene, and 80 mL of tetrahydrofuran were added. Then, 8.2 g (0.11 mole) of butylamine was added dropwise under stirring. After the completion of addition, the resultant mixture was stirred overnight at room temperature. The mixture was neutralized and separated into liquid layers with 150 mL of 5% hydrochloric acid, and then an organic layer was washed two times with 150 mL of brine. The solvent was distilled off, and the resultant oily substance was recrystallized from a mixed solvent of 80 mL of methanol and 80 mL of water. The resultant solid was dried to produce 20.9 g of a compound represented by formula (A-3).

In a reactor provided with a stirrer and a thermometer, 20.9 g (0.086 mole) of the compound represented by the formula (A-3), 23.8 g (0.095 mole) of 4-(3-acryloyloxypropyloxy)benzoic acid (compound represented by formula (A-4)), 0.53 g (4.3 millimole) of N,N-dimethylaminopyridine, and 119 mL of dichloromethane were added and stirred under ice cooling. Then, 13.1 g (0.10 mole) of N,N'-diisopropylcarbodiimide was added dropwise while the temperature of the reaction solution was kept at 15° C. or less. After the completion of addition, reaction was performed by stirring at room temperature for 6 hours. The reaction solution was filtered to remove precipitates, and then the solvent was distilled off. The resultant solid was dissolved in dichloromethane and purified by column chromatography (purifying agent: silica gel 41 g, eluent: dichloromethane 328 mL), and then the solvent was distilled off. The resultant solid was recrystallized two times from a mixed solvent of 41 mL of dichloromethane and 123 mL of methanol and then dried to produce 33.6 g of the target compound represented by formula (I-1).

(Physical Property Values of Compound Represented by Formula (I-1))

$^1$H NMR (CDCl$_3$) δ 2.19-2.25 (m, 5H), 2.34 (s, 3H), 4.17 (t, 2H), 4.39 (t, 2H), 5.85 (dd, 1H), 6.14 (dd, 1H), 6.42 (dd, 1H), 6.98-7.08 (m, 5H), 7.36 (d, 2H), 8.16 (d, 2H), 8.29 (d, 2H) ppm.

$^{13}$C NMR (CDCl$_3$) δ 16.1, 20.8, 28.5, 61.1, 64.7, 113.1, 114.3, 121.3, 121.6, 122.0, 127.0, 127.5, 128.2, 129.8, 131.0, 131.7, 131.8, 132.4, 135.6, 147.2, 155.2, 163.3, 164.2, 164.3, 166.1 ppm.

LRMS (EI) m/z 474 (100).

(Example 2) Production of Compound Represented by Formula (I-2)

[Chem. 21]

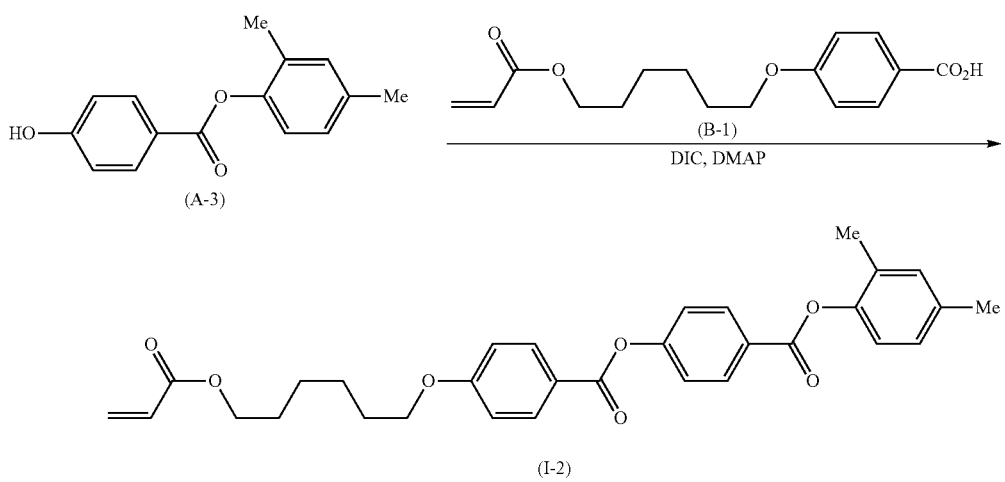

In a reactor provided with a stirrer and a thermometer, 25.1 g (0.10 mole) of a compound represented by formula (A-3), 33.3 g (0.11 mole) of 4-(6-acryloyloxy-hexyloxy) benzoic acid (compound represented by formula (B-1)), 0.63 g (5.2 millimole) of N, N-dimethylaminopyridine, and 166 mL of dichloromethane were added and stirred under ice cooling. Then, 15.7 g (0.12 mole) of N,N'-diisopropylcarbodiimide was added dropwise while the temperature of the reaction solution was kept at 15° C. or less. After the completion of addition, reaction was performed by stirring at room temperature for 5 hours. The reaction solution was filtered to remove precipitates, and then the solvent was distilled off. The resultant solid was dissolved in dichloromethane and purified by column chromatography (purifying agent: silica gel 53 g, eluent: dichloromethane 430 mL), and then the solvent was distilled off. The resultant solid was recrystallized two times from a mixed solvent of 53 mL of dichloromethane and 159 mL of methanol and then dried to produce 42.8 g of the target compound represented by formula (I-2).

(Physical Property Values of Compound Represented by Formula (I-2))

$^1$H NMR (CDCl$_3$) δ 1.45-1.57 (m, 4H), 1.73 (quin, 2H), 1.85 (quin, 2H), 2.19 (s, 3H), 2.34 (s, 3H), 4.06 (t, 2H), 4.18 (t, 2H), 5.82 (dd, 1H), 6.12 (dd, 1H), 6.41 (dd, 1H), 6.97-7.08 (m, 5H), 7.36 (d, 2H), 8.15 (d, 2H), 8.29 (d, 2H) ppm.

$^{13}$C NMR (CDCl$_3$) δ 16.1, 20.8, 25.6, 25.7, 28.5, 28.9, 64.4, 68.1, 114.3, 121.0, 121.6, 122.0, 126.9, 127.2, 127.5, 128.5, 129.8, 130.5, 131.7, 131.8, 132.4, 135.6, 147.2, 155.2, 163.7, 164.3, 164.3, 166.3 ppm.

LRMS (EI) m/z 516 (100).

(Example 3) Production of Compound Represented by Formula (I-3)

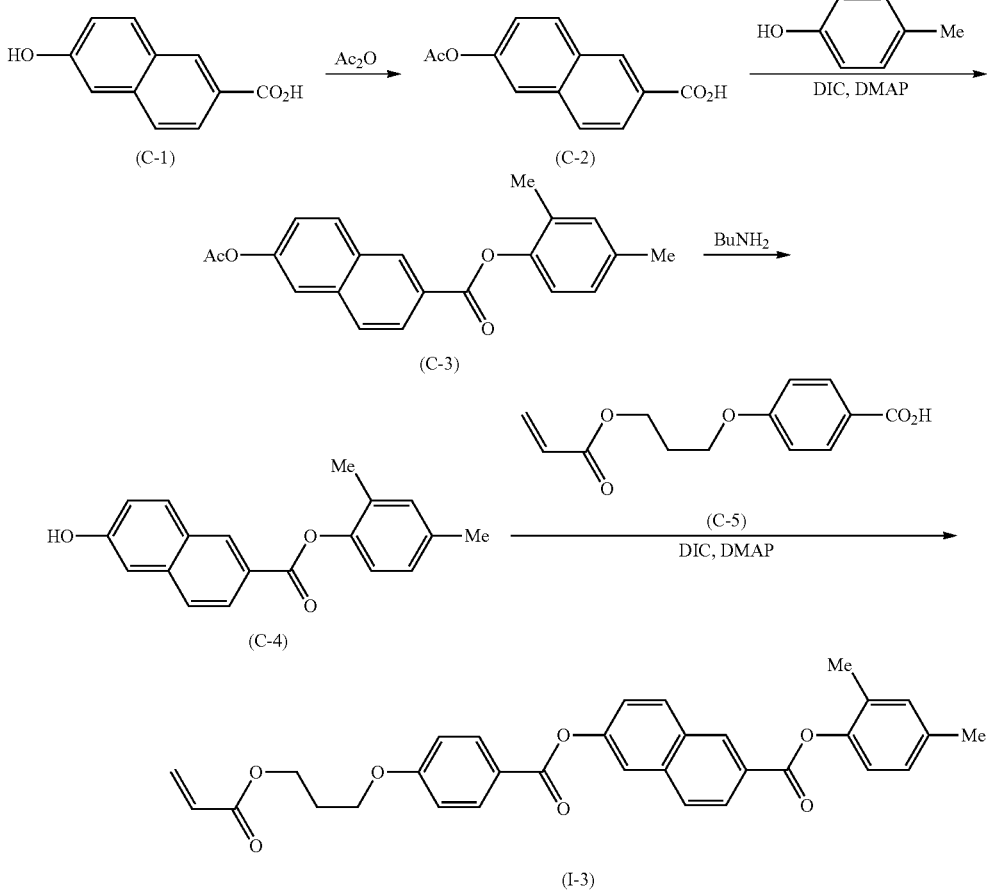

In a reactor provided with a stirrer, a condenser, and a thermometer, 100 g (0.53 mole) of 6-hydroxy-2-naphthoic acid (compound represented by formula (C-1)), 300 mL of acetic acid, 65.1 g (0.64 mole) of acetic anhydride, and 5 g of sulfuric acid were added and reacted by heating at 60° C. for 8 hours. Then, 1 L of water was added to the reaction solution and stirred for 1 hour under ice cooling, and then the precipitated solid was filtered off. The resultant solid was dispersed and washed two times with 1 L of water. The solid was dried to produce 118.7 g of a compound represented by formula (C-2).

In a reactor provided with a stirrer and a thermometer, 25.0 g (0.11 mole) of the compound represented by the formula (C-2), 12.1 g (0.099 mole) of 2,4-dimethylphenol, 0.6 g (4.9 millimole) of N,N-dimethylaminopyridine, and 125 mL of dichloromethane were added and stirred under ice cooling. Then, 15.0 g (0.12 mole) of N,N'-diisopropylcarbodiimide was added dropwise while the temperature of the reaction solution was kept at 15° C. or less. After the completion of addition, reaction was performed by stirring at room temperature for 5 hours. The reaction solution was filtered to remove precipitates, and then the solvent was distilled off. The resultant solid was dissolved in dichloromethane and purified by column chromatography (purifying agent: silica gel 33 g, eluent: dichloromethane 264 mL), and then the solvent was distilled off. The resultant solid was dispersed and washed with 99 mL of methanol and then dried to produce 30.7 g of a compound represented by formula (C-3).

In a reactor provided with a stirrer and a thermometer, 30.7 g (0.092 mole) of the compound represented by the formula (C-3), 92 mL of toluene, and 92 mL of tetrahydrofuran were added. Then, 8.1 g (0.11 mole) of butylamine was added dropwise under stirring. After the completion of addition, stirring was performed overnight at room temperature. The reaction solution was neutralized and separated into liquid layers with 150 mL of 5% hydrochloric acid, and then an organic layer was washed two times with 150 mL of brine. The solvent was distilled off, and the resultant oily substance was recrystallized from a mixed solvent of 66 mL of methanol and 66 mL of water. The resultant solid was dried to produce 24.2 g of a compound represented by formula (C-4).

In a reactor provided with a stirrer and a thermometer, 24.2 g (0.083 mole) of the compound represented by the formula (C-4), 22.7 g (0.091 mole) of 4-(3-acryloyloxypropyloxy)benzoic acid (compound represented by formula (C-5)), 0.50 g (4.1 millimole) of N,N-dimethylaminopyridine, and 114 mL of dichloromethane were added and stirred under ice cooling. Then, 12.5 g (0.099 mole) of N,N'-diisopropylcarbodiimide was added dropwise while the temperature of the reaction solution was kept at 15° C. or less. After the completion of addition, reaction was performed by stirring at room temperature for 6 hours. The reaction solution was filtered to remove precipitates, and then the solvent was distilled off. The resultant solid was dissolved in dichloromethane and purified by column chromatography (purifying agent: silica gel 44 g, eluent: dichloromethane 352 mL), and then the solvent was distilled off. The resultant solid was recrystallized two times from a mixed solvent of 44 mL of dichloromethane and 132 mL of methanol and then dried to produce 36.8 g of the target compound represented by formula (I-3).

(Physical Property Values of Compound Represented by Formula (I-3))

$^1$H NMR (CDCl$_3$) δ 2.20-2.26 (m, 5H), 2.35 (s, 3H), 4.18 (t, 2H), 4.40 (t, 2H), 5.85 (dd, 1H), 6.14 (dd, 1H), 6.43 (dd, 1H), 7.01 (d, 2H), 7.07 (s, 2H), 7.11 (s, 1H), 7.46 (dd, 1H), 7.77 (d, 1H), 7.93 (d, 1H), 8.06 (d, 1H), 8.20 (d, 2H), 8.24 (dd, 1H), 8.82 (d, 1H) ppm.

$^{13}$C NMR (CDCl$_3$) δ 16.2, 20.8, 28.5, 61.1, 64.7, 114.3, 118.8, 121.6, 121.6, 122.5, 126.2, 126.6, 127.5, 128.1, 128.2, 129.8, 130.4, 131.0, 131.6, 131.8, 132.4, 135.7, 136.4, 147.3, 150.8, 163.2, 164.7, 165.0, 166.1 ppm.

LRMS (EI) m/z 524 (100).

(Example 4) Production of Compound Represented by Formula (I-4)

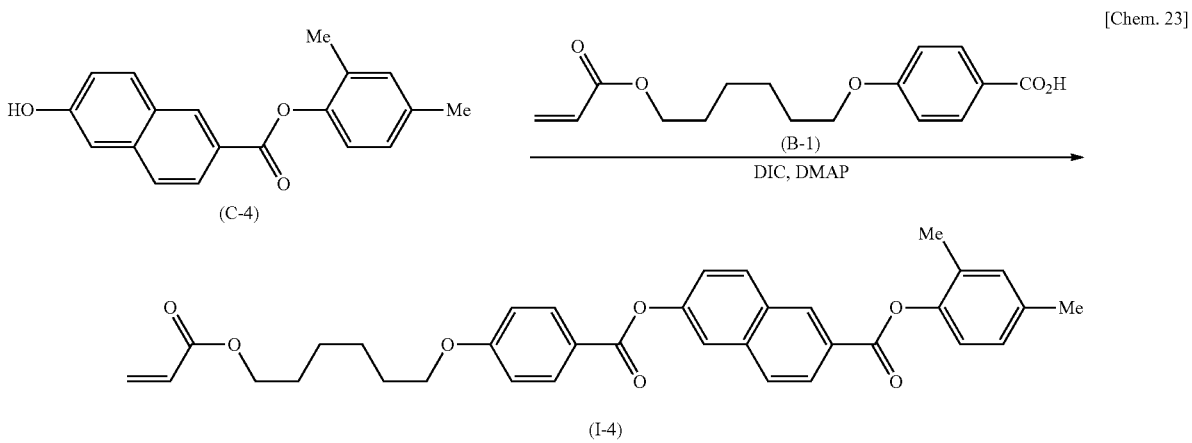

[Chem. 23]

In a reactor provided with a stirrer and a thermometer, 25.0 g (0.086 mole) of the compound represented by the formula (C-4), 27.5 g (0.094 mole) of 4-(6-acryloyloxyhexyloxy)benzoic acid (compound represented by formula (B-1)), 0.52 g (4.3 millimole) of N,N-dimethylaminopyridine, and 138 mL of dichloromethane were added and stirred under ice cooling. Then, 13.0 g (0.10 mole) of N,N'-diisopropylcarbodiimide was added dropwise while the temperature of the reaction solution was kept at 15° C. or less. After the completion of addition, reaction was performed by stirring at room temperature for 8 hours. The reaction solution was filtered to remove precipitates, and then the solvent was distilled off. The resultant solid was dissolved in dichloromethane and purified by column chromatography (purifying agent: silica gel 49 g, eluent: dichloromethane 392 mL), and then the solvent was distilled off. The resultant solid was recrystallized two times from a mixed solvent of 49 mL of dichloromethane and 147 mL of methanol and then dried to produce 39.3 g of the target compound represented by formula (I-4).

(Physical Property Values of Compound Represented by Formula (I-4))

$^1$H NMR (CDCl$_3$) δ 1.45-1.56 (m, 4H), 1.73 (quin, 2H), 1.86 (quin, 2H), 2.23 (s, 3H), 2.35 (s, 3H), 4.07 (t, 2H), 4.19 (t, 2H), 5.82 (dd, 1H), 6.13 (dd, 1H), 6.41 (dd, 1H), 7.00 (dd, 2H), 7.06 (s, 2H), 7.11 (s, 1H), 7.46 (dd, 1H), 7.77 (d, 1H), 7.93 (d, 1H), 8.06 (d, 1H), 8.19 (d, 2H), 8.23 (dd, 1H), 8.81 (s, 1H) ppm.

$^{13}$C NMR (CDCl$_3$) δ 16.2, 20.8, 25.7, 25.7, 28.5, 28.9, 64.4, 68.1, 114.3, 118.8, 121.2, 121.6, 122.5, 126.2, 126.6, 127.5, 128.1, 128.5, 129.8, 130.4, 130.5, 131.0, 131.6, 131.8, 132.4, 135.7, 136.4, 147.3, 150.9, 163.6, 164.8, 165.0, 166.3 ppm.

LRMS (EI) m/z 566 (100).

(Example 5) Production of Compound Represented by Formula (I-7)

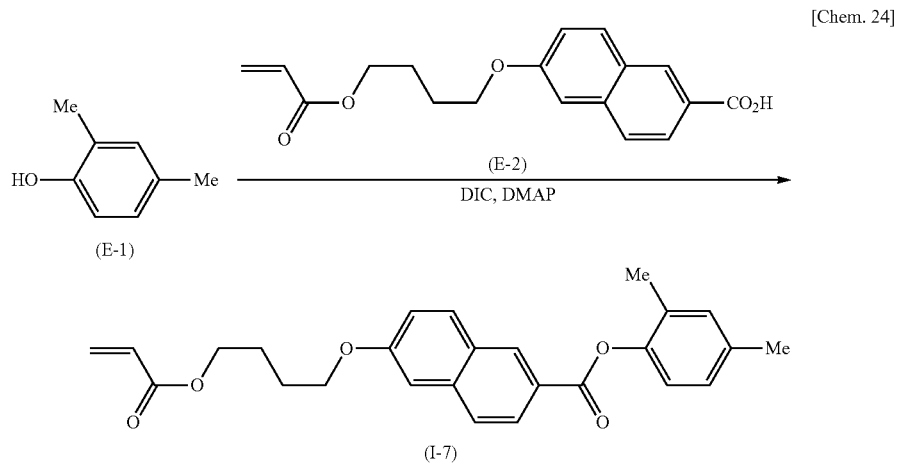

In a reactor provided with a stirrer and a thermometer, 14.1 g (0.12 mole) of 2,4-dimethylphenol (compound represented by the formula (E-1)), 40.0 g (0.13 mole) of 6-(4-acryloyloxy-butyloxy)-2-naphthoic acid (compound represented by formula (E-2)), 0.71 g (5.8 millimole) of N,N-dimethylaminopyridine, and 200 mL of dichloromethane were added and stirred under ice cooling. Then, 17.5 g (0.14 mole) of N,N'-diisopropylcarbodiimide was added dropwise while the temperature of the reaction solution was kept at 15° C. or less. After the completion of addition, reaction was performed by stirring at room temperature for 10 hours. The reaction solution was filtered to remove precipitates, and then the solvent was distilled off. The resultant solid was dissolved in dichloromethane and purified by column chromatography (purifying agent: silica gel 48 g, eluent: dichloromethane 384 mL), and then the solvent was distilled off. The resultant solid was recrystallized two times from a mixed solvent of 48 mL of dichloromethane and 144 mL of methanol and then dried to produce 41.2 g of the target compound represented by formula (I-7).

(Physical Property Values of Compound Represented by Formula (I-7))

$^1$H NMR (CDCl$_3$) δ 2.22 (s, 3H), 2.25 (quin, 2H), 2.34 (s, 3H), 4.23 (t, 2H), 4.42 (t, 2H), 5.85 (dd, 1H), 6.15 (dd, 1H), 6.43 (dd, 1H), 7.03-7.09 (m, 3H), 7.22 (dd, 2H), 7.80 (d, 1H), 7.89 (d, 1H), 8.17 (dd, 1H), 8.71 (s, 1H) ppm.

$^{13}$C NMR (CDCl$_3$) δ 16.2, 20.8, 28.5, 61.3, 64.5, 106.4, 119.9, 121.7, 124.5, 126.2, 127.0, 127.5, 127.9, 128.3, 129.9, 130.9, 131.0, 131.5, 131.7, 135.5, 137.4, 147.4, 158.9, 165.3, 166.1 ppm.

LRMS (EI) m/z 418 (100).

(Example 6) Production of Compound Represented by Formula (I-5)

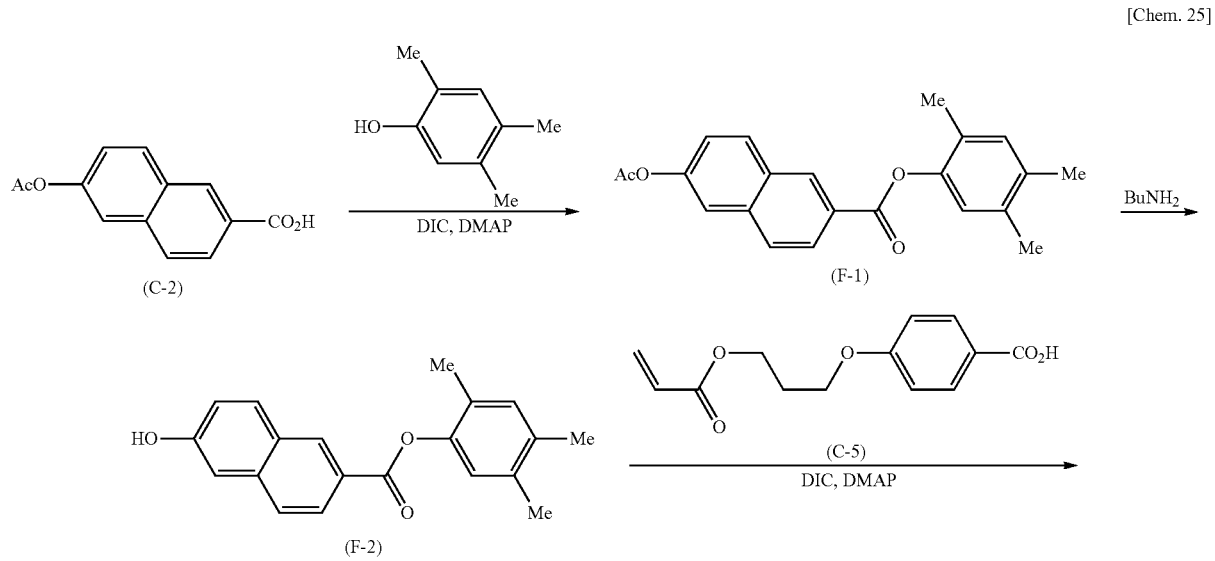

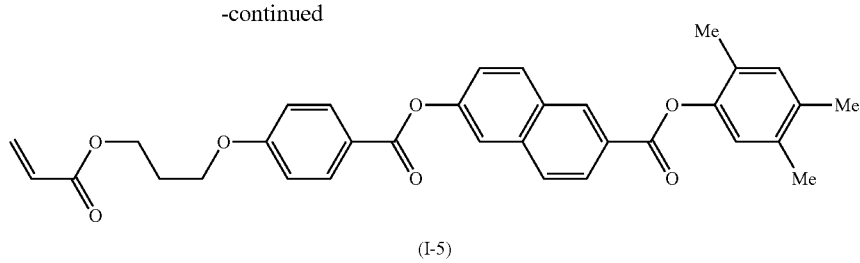

(I-5)

A compound represented by formula (I-5) was synthesized through the same synthesis route as in Example 3 except that 2,4-dimethylphenol was changed to 2,4,5-trimethylphenol (compound represented by formula (F-2)).
(Physical Property Values of Compound Represented by Formula (I-5))

$^1$H NMR (CDCl$_3$) δ 2.20-2.26 (m, 7H), 2.35 (s, 3H), 4.18 (t, 2H), 4.40 (t, 2H), 5.85 (dd, 1H), 6.14 (dd, 1H), 6.43 (dd, 1H), 7.01 (d, 2H), 7.07 (s, 2H), 7.11 (s, 1H), 7.46 (dd, 1H), 7.77 (d, 1H), 8.06 (d, 1H), 8.20 (d, 2H), 8.24 (dd, 1H), 8.82 (d, 1H) ppm.

$^{13}$C NMR (CDCl$_3$) δ 16.2, 20.8, 28.5, 61.1, 61.5, 64.7, 114.3, 118.8, 121.6, 121.6, 122.5, 126.2, 126.6, 127.5, 128.1, 128.2, 129.8, 130.4, 131.0, 131.8, 132.4, 135.7, 136.4, 147.3, 150.8, 163.2, 164.7, 165.0, 166.1 ppm.

LRMS (EI) m/z 538 (100).

(Example 7) Production of Compound Represented by Formula (I-11)

[Chem. 26]

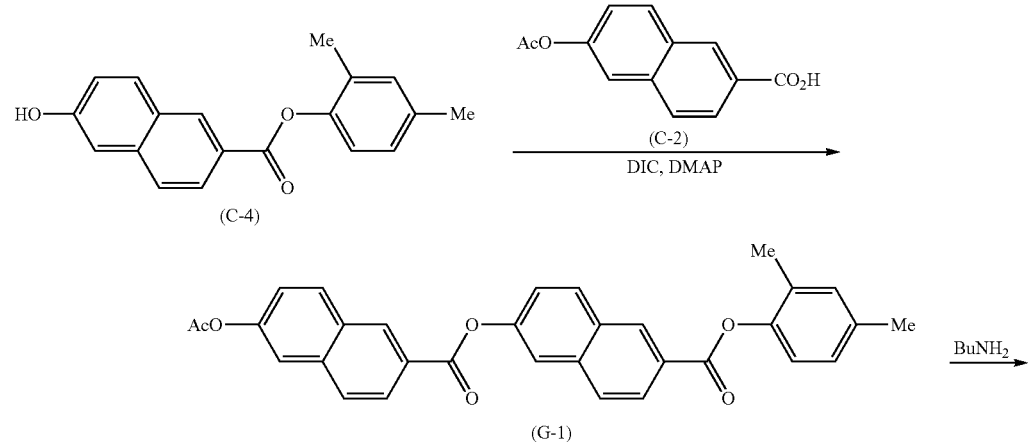

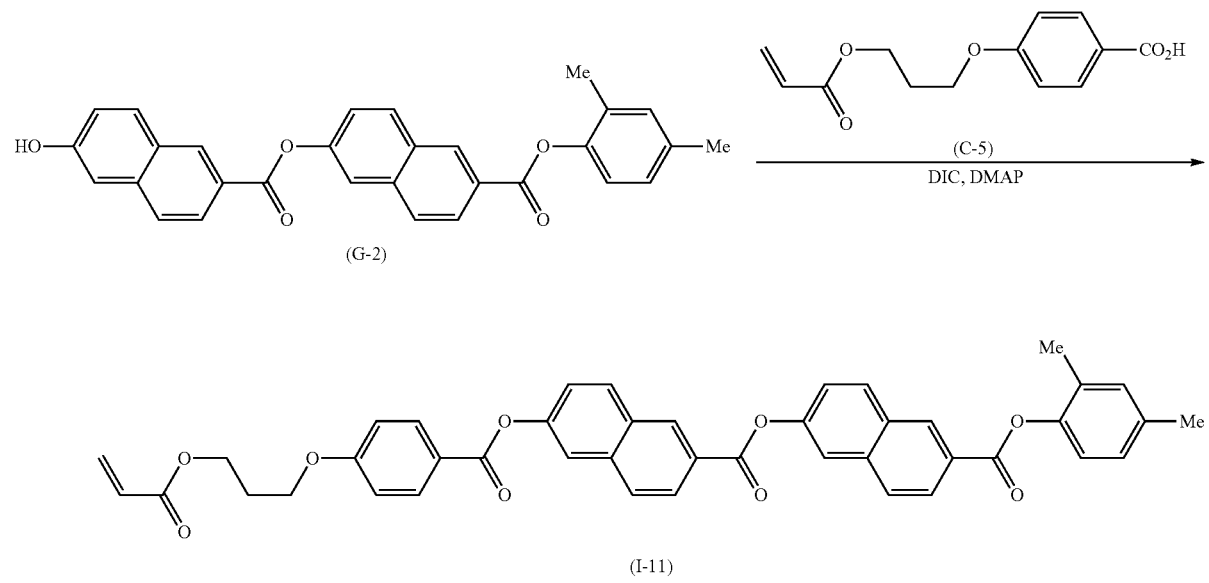

(I-11)

In a flask provided with a stirrer and a thermometer, 34.6 g (0.12 mole) of a compound represented by formula (C-4), 30.0 g (0.13 mole) of a compound represented by formula (C-2), and 0.72 g (5.9 millimole) of N,N-dimethylaminopyridine were added and suspended in 150 mL of dichloromethane. Then, 17.9 g (0.14 mole) of N,N'-diisopropylcarbodiimide was added dropwise under stirring. After the completion of addition, reaction was performed by stirring at room temperature for 10 hours. The reaction solution was filtered to remove precipitates, and then the solvent was distilled off. The resultant solid was dissolved in dichloromethane and purified by column chromatography (purifying agent: silica gel 60 g, eluent: dichloromethane 480 mL), and then the solvent was distilled off. The resultant solid was recrystallized with a mixed solvent of 60 mL of dichloromethane and 180 mL of methanol and then dried to produce 52.6 g of a compound represented by formula (G-1).

In a reactor provided with a stirrer and a thermometer, 52.6 g (0.10 mole) of the compound represented by the formula (G-1), 157 mL of toluene, and 157 mL of tetrahydrofuran were added. Then, 9.1 g (0.12 mole) of butylamine was added dropwise under stirring. After the completion of addition, stirring was performed overnight at room temperature. The reaction solution was neutralized and separated into liquid layers with 150 mL of 5% hydrochloric acid, and then an organic layer was washed two times with 150 mL of brine. The solvent was distilled off, and a target product was isolated by flash chromatography (silica gel, dichloromethane/hexane). The resultant compound was recrystallized from a mixed solvent of 50 mL of methanol and 50 mL of water. The resultant solid was dried to produce 14.5 g of a compound represented by formula (G-2).

In a reactor provided with a stirrer and a thermometer, 14.5 g (0.031 mole) of the compound represented by the formula (G-2), 8.61 g (0.034 mole) of 4-(3-acryloyloxypropyloxy)benzoic acid (compound represented by formula (C-5)), 0.19 g (1.6 millimole) of N,N-dimethylaminopyridine, and 43 mL of dichloromethane were added and stirred under ice cooling. Then, 4.74 g (0.038 mole) of N,N'-diisopropylcarbodiimide was added dropwise while the temperature of the reaction solution was kept at 15° C. or less. After the completion of addition, reaction was performed by stirring at room temperature for 6 hours. The reaction solution was filtered to remove precipitates, and then the solvent was distilled off. The resultant solid was dissolved in dichloromethane and purified by column chromatography (purifying agent: silica gel 22 g, eluent: dichloromethane 176 mL), and then the solvent was distilled off. The resultant solid was recrystallized two times from a mixed solvent of 22 mL of dichloromethane and 66 mL of methanol and then dried to produce 19.6 g of the target compound represented by formula (I-11).

(Physical Property Values of Compound Represented by Formula (I-11))

$^1$H NMR (CDCl$_3$) δ 2.20-2.26 (m, 5H), 2.35 (s, 3H), 4.18 (t, 2H), 4.40 (t, 2H), 5.86 (dd, 1H), 6.15 (dd, 1H), 6.43 (dd, 1H), 7.01 (d, 2H), 7.09 (d, 3H), 7.49 (dd, 1H), 7.54 (dd, 1H), 7.83 (dd, 2H), 7.97 (d, 2H), 8.10 (dd, 2H), 8.21 (d, 2H), 8.27 (dd, 2H), 8.86 (d, 2H) ppm.

$^{13}$C NMR (CDCl$_3$) δ 16.2, 20.9, 28.5, 61.1, 64.7, 114.4, 118.9, 118.9, 121.6, 121.7, 122.4, 122.7, 126.2, 126.3, 126.8, 127.6, 128.2, 128.2, 128.3, 129.9, 130.5, 130.6, 131.0, 131.1, 131.2, 131.7, 131.8, 131.9, 132.5, 135.7, 136.5, 136.6, 147.3, 150.8, 151.1, 163.3, 164.7, 165.1, 165.1, 166.1 ppm.

LRMS (EI) m/z 694 (100).

(Example 8) Production of Compound Represented by Formula (I-13)

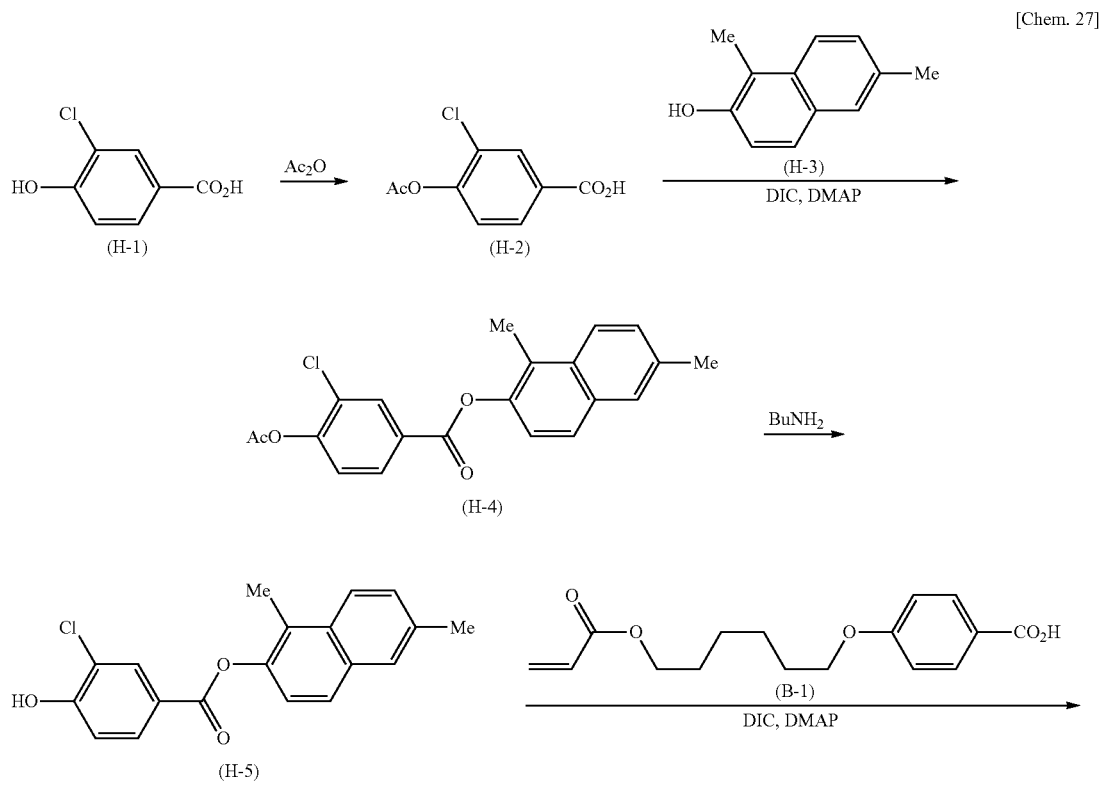

[Chem. 27]

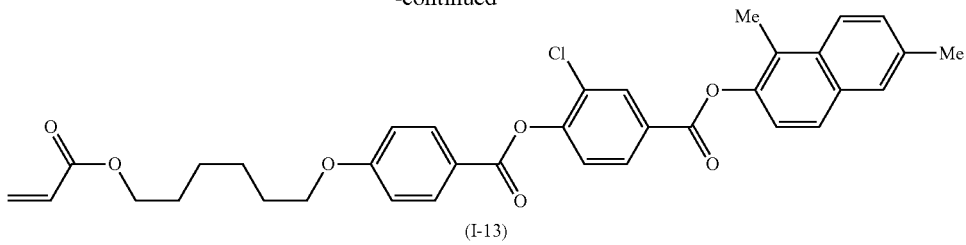

(I-13)

In a reactor provided with a stirrer, a condenser, and a thermometer, 50.0 g (0.29 mole) of 3-chloro-4-hydroxybenzoic acid (compound represented by formula (H-1)), 150 mL of acetic acid, 44.4 g (0.44 mole) of acetic anhydride, and 2.5 g of sulfuric acid were added and reacted by heating at 60° C. for 8 hours. Then, 1 L of water was added to the reaction solution and stirred for 1 hour under ice cooling, and then the precipitated solid was filtered off. The resultant solid was dispersed and washed two times with 1 L of water. The solid was dried to produce 59.1 g of a compound represented by formula (H-2).

In a reactor provided with a stirrer and a thermometer, 59.1 g (0.28 mole) of the compound represented by the formula (H-2), 43.1 g (0.25 mole) of 1,6-dimethyl-2-naphthol (compound represented by formula (H-3)), 3.1 g (25 millimole) of N,N-dimethylaminopyridine, and 250 mL of dichloromethane were added and stirred under ice cooling. Then, 37.9 g (0.30 mole) of N,N'-diisopropylcarbodiimide was added dropwise while the temperature of the reaction solution was kept at 15° C. or less. After the completion of addition, reaction was performed by stirring at room temperature for 5 hours. The reaction solution was filtered to remove precipitates, and then the solvent was distilled off. The resultant solid was dissolved in dichloromethane and purified by column chromatography (purifying agent: silica gel 90 g, eluent: dichloromethane 900 mL), and then the solvent was distilled off. The resultant solid was dispersed and washed with 180 mL of methanol and then dried to produce 84.8 g of a compound represented by formula (H-4).

In a reactor provided with a stirrer and a thermometer, 84.8 g (0.23 mole) of the compound represented by the formula (H-4), 240 mL of toluene, and 240 mL of tetrahydrofuran were added. Then, 25.2 g (0.35 mole) of butylamine was added dropwise under stirring. After the completion of addition, stirring was performed overnight at room temperature. The reaction solution was neutralized and separated into liquid layers with 300 mL of 5% hydrochloric acid, and then an organic layer was washed two times with 300 mL of brine. The solvent was distilled off, and the resultant oily substance was recrystallized from a mixed solvent of 150 mL of methanol and 150 mL of water. The resultant solid was dried to produce 61.6 g of a compound represented by formula (H-5).

In a reactor provided with a stirrer and a thermometer, 20.0 g (0.061 mole) of the compound represented by the formula (H-5), 19.7 g (0.067 mole) of 4-(6-acryloyloxyhexyloxy)benzoic acid (compound represented by formula (B-1)), 0.70 g (5.7 millimole) of N,N-dimethylaminopyridine, and 100 mL of dichloromethane were added and stirred under ice cooling. Then, 9.3 g (0.074 mole) of N,N'-diisopropylcarbodiimide was added dropwise while the temperature of the reaction solution was kept at 15° C. or less. After the completion of addition, reaction was performed by stirring at room temperature for 6 hours. The reaction solution was filtered to remove precipitates, and then the solvent was distilled off. The resultant solid was dissolved in dichloromethane and purified by column chromatography (purifying agent: silica gel 37 g, eluent: dichloromethane 370 mL), and then the solvent was distilled off. The resultant solid was recrystallized two times from a mixed solvent of 37 mL of dichloromethane and 111 mL of methanol and then dried to produce 29.4 g of the target compound represented by formula (I-13).

(Physical Property Values of Compound Represented by Formula (I-13))

$^1$H NMR (CDCl$_3$) δ 1.29 (m, 4H), 1.57 (quin, 2H), 1.71 (quin, 2H), 2.46 (s, 3H), 2.65 (s, 3H), 3.94 (t, 2H), 4.15 (t, 2H), 5.80 (dd, 1H), 6.05 (dd, 1H), 6.43 (dd, 1H), 6.83 (d, 1H), 6.92 (d, 2H), 7.15 (d, 1H), 7.24 (d, 1H), 7.43 (d, 1H), 7.39 (s, 1H), 7.57 (d, 1H), 8.03 (d, 2H), 8.09 (d, 1H), 8.22 (s, 1H) ppm.

$^{13}$C NMR (CDCl$_3$) δ 9.2, 21.3, 26.3, 26.5, 30.0, 30.6, 66.8, 72.3, 114.1, 114.1, 114.9, 118.0, 121.4, 122.2, 122.7, 126.6, 126.7, 127.4, 127.9, 128.6, 128.6, 128.6, 128.8, 130.3, 130.7, 130.7, 130.9, 131.4, 132.1, 152.6, 158.7, 164.0, 164.0, 164.0, 165.0 ppm.

LRMS (EI) m/z 600 (100)

Example 9

[Chem. 28]

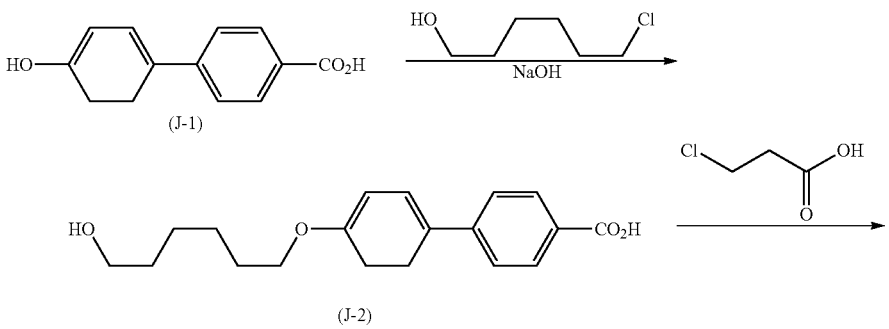

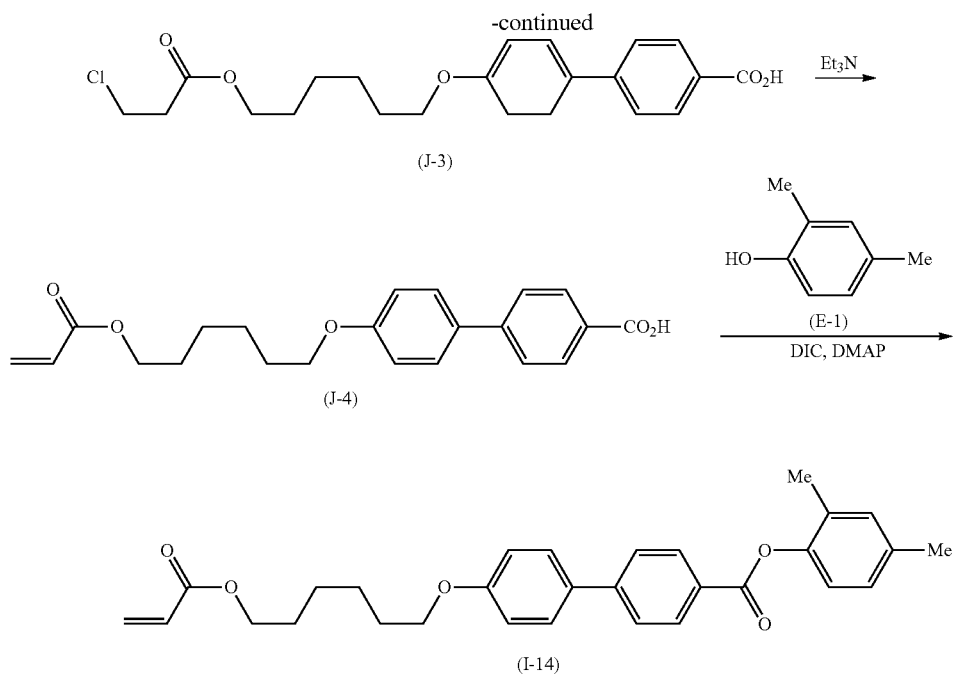

In a reactor provided with a stirrer and a thermometer, 20.0 g (0.093 mole) of 4'-hydroxybiphenyl-4-carboxylic acid, 15.3 g (0.11 mole) of 6-chlorohexanol, 160 mL of ethanol, and 80 mL of a 10% aqueous sodium hydroxide solution were added and stirred under heating at 78° C. for 10 hours. The mixture was allowed to cool to room temperature and then neutralized by adding 10% hydrochloric acid. The reaction solution was subjected to extraction with ethyl acetate and then purified by column chromatography and recrystallization to produce 14.6 g (0.046 mole) of a compound represented by formula (J-2).

In a flask provided with a stirrer and a Dean-Stark apparatus, 14.6 g (0.046 mole) of the compound represented by formula (J-2), 7.56 g (0.070 mole) of 3-chloropropionic acid, 0.88 g (4.6 millimole) of toluenesulfonic acid monohydrate, and 200 mL of toluene were added and heated under reflux for 6 hours while water was appropriately removed. The mixture was allowed to cool to room temperature, then subjected to extraction with ethyl acetate, and purified by column chromatography and recrystallization to produce 11.3 g (0.028 mole) of a compound represented by formula (J-3).

In a reactor provided with a stirrer and a thermometer, 11.3 g (0.028 mole) of the compound represented by the formula (J-3), 5.67 g (0.056 mole) of triethylamine, and 110 mL of tetrahydrofuran were added. The resultant mixture was heated at 66° C. for 10 hours, then allowed to cool to room temperature, and then neutralized with hydrochloric acid. The product was purified by column chromatography and recrystallization to produce 7.22 g (0.020 mole) of a compound represented by formula (J-4).

In a reactor provided with a stirrer and a thermometer, 7.22 g (0.020 mole) of 4'-(6-acryloyloxy-hexyloxy)-4-biphenylcarboxylic acid (compound represented by the formula (J-4)), 2.39 g (0.20 mole) of 2,4-dimethylphenol (compound represented by formula (E-1)), 0.24 g (1.9 millimole) of N,N-dimethylaminopyridine, and 50 mL of dichloromethane were added and stirred under ice cooling. Then, 2.97 g (0.024 mole) of N,N'-diisopropylcarbodiimide was added dropwise while the temperature of the reaction solution was kept at 15° C. or less. After the completion of addition, reaction was performed by stirring at room temperature for 7 hours. The reaction solution was filtered to remove precipitates, and then the solvent was distilled off. The resultant solid was dissolved in dichloromethane and purified by column chromatography (purifying agent: silica gel 20 g, eluent: dichloromethane 200 mL), and then the solvent was distilled off. The resultant solid was recrystallized two times from a mixed solvent of 10 mL of dichloromethane and 100 mL of methanol and then dried to produce 5.2 g of the target compound represented by formula (I-14).

(Physical Property Values of Compound Represented by Formula (I-14))

$^1$H NMR (CDCl$_3$) δ 1.44-1.56 (m, 4H), 1.73 (quin, 7.3 Hz, 2H), 1.84 (quin, 7.3 Hz, 2H), 2.21 (s, 3H), 2.34 (s, 3H), 4.02 (t, 6.5 Hz, 2H), 4.18 (t, 6.5 Hz, 2H), 5.82 (dd, 1.4, 10.4 Hz, 1H), 6.13 (dd, 10.4, 17.4 Hz, 1H), 6.41 (dd, 1.6, 17.3 Hz, 1H), 6.98-7.09 (m, 5H), 7.59 (d, 8.9 Hz, 2H), 7.69 (d, 8.9 Hz, 2H), 8.25 (d, 8.11 Hz, 2H) ppm.

$^{13}$C NMR (CDCl$_3$) δ 16.2, 20.9, 25.7, 25.7, 28.6, 29.1, 64.5, 67.9, 114.9, 121.7, 126.6, 127.5, 128.4, 128.6, 129.9, 130.6, 130.6, 130.7, 131.8, 132.1, 135.6, 145.9, 147.3, 159.4, 165.0, 166.3 ppm.

LRMS (EI) m/z 472 (100).

Examples 10 to 15, Comparative Examples 1 to 5

Table 1 below describes the physical property values of the compound (I-1) to the compound (I-4), the compound (I-7), and the compound (I-9) of the present invention described in Examples 1 to 5, comparative compound 1 and comparative compound 2 described in EP1786887B1, and comparative compound 3 described in GB2280445A.

[Chem. 29]

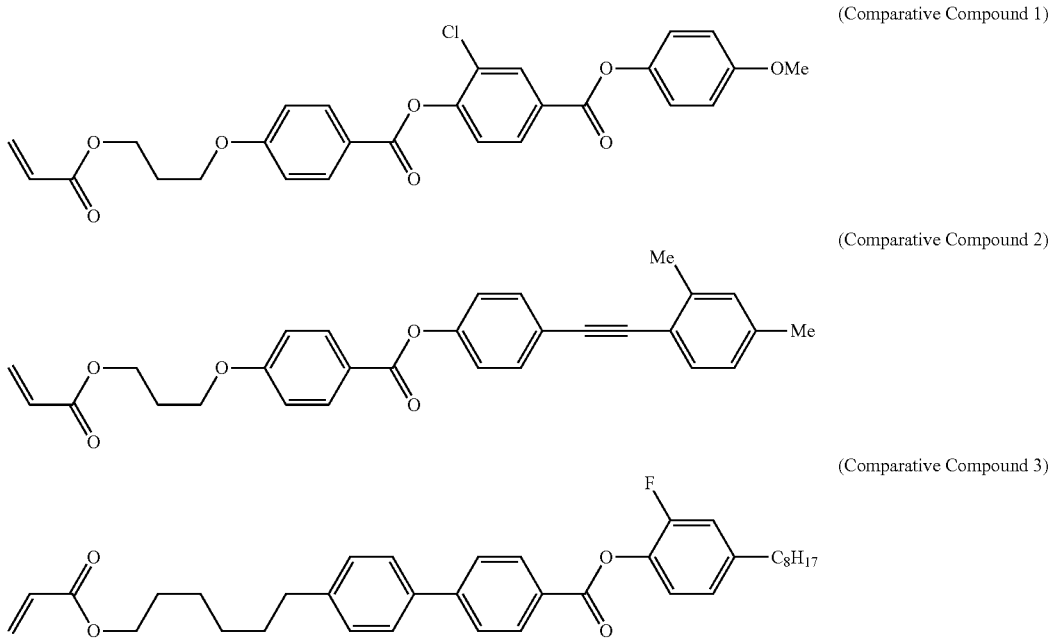

(Comparative Compound 1)

(Comparative Compound 2)

(Comparative Compound 3)

TABLE 1

| | Transition temperature | | | Refractive index anisotropy | Maximum concentration added |
|---|---|---|---|---|---|
| Compound (I-1) | C 112 | N | 142 I | 0.184 | >60% |
| Compound (I-2) | C 94 | N | 131 I | 0.174 | 50% |
| Compound (I-3) | C 126 | N | 215 I | 0.233 | 50% |
| Compound (I-4) | C 117 | N | 194 I | 0.225 | 40% |
| Compound (I-7) | C 78 | I | | 0.173 | >60% |
| Compound (I-9) | C 62 | N | 124 I | 0.237 | >60% |
| Comparative Compound 1 | C 101 | N | 159 I | 0.189 | 30% |
| Comparative Compound 2 | C 92 | N | 166 I | 0.258 | 40% |
| Comparative Compound 3 | C 83 | N | 157 I | 0.176 | 20% |

The compound (I-1) to the compound (I-4) and the compound (I-9) of the present invention show a nematic liquid crystal phase over a wide temperature region, and are thus expected to have the effect of stabilizing a liquid crystal phase of a composition by being added to the composition. It is also found that the compound (I-1) to the compound (I-4), the compound (I-7), and the compound (I-9) have smaller refractive index anisotropy than the comparative compound 2.

In order to evaluate storage stability of the compounds, a polymerizable liquid crystal composition was prepared by adding each of the compounds in increments of 5% from 10% to 60% to a mother liquid crystal composed of compound VI (30%), compound VII (30%), compound VIII (30%), and compound IX (10%). Table 1 shows the maximum concentration added without causing precipitation of crystals after each of the prepared polymerizable liquid crystal compositions was allowed to stand at 25° C. for 10 hours. It is found that all of the compound (I-1) to the compound (I-3), the compound (I-7), and the compound (I-9) of the present invention show the high maximum concentration added without causing precipitation of crystals and thus show high storage stability as compared with the comparative compound 1 and the comparative compound 3. It is also found that the compound (I-4) of the present invention shows high storage stability equivalent to the comparative compound 2.

[Chem. 30]

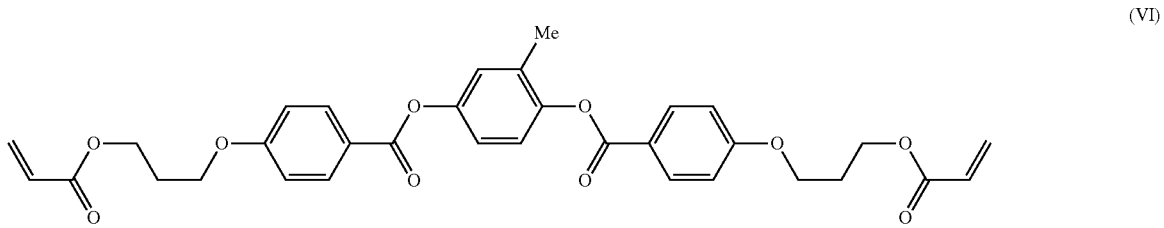

(VI)

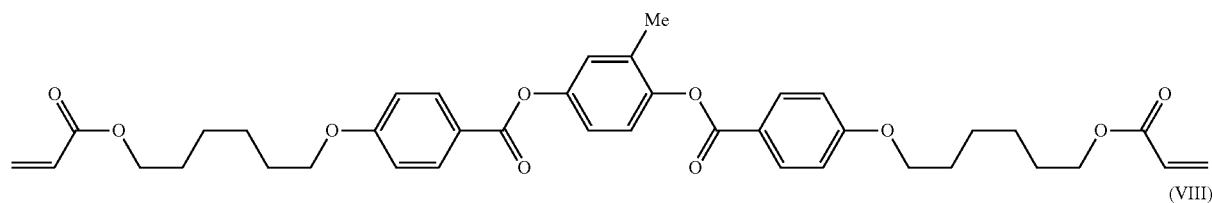

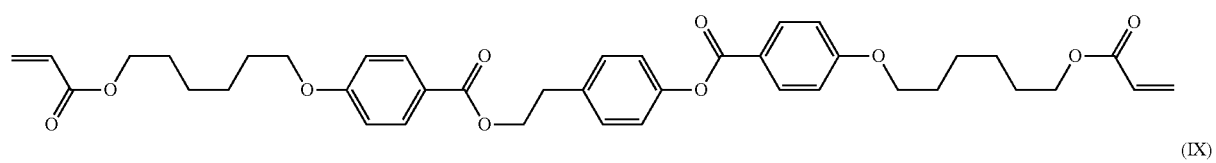

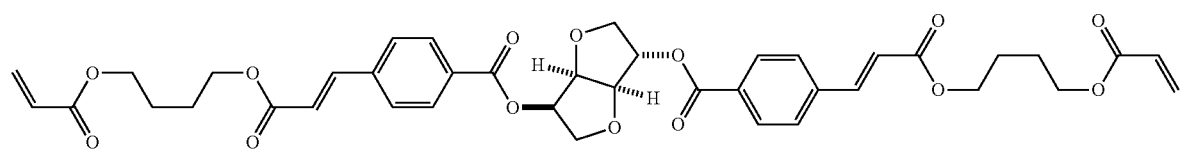

Polymerizable liquid crystal compositions containing the compound (I-1) to the compound (I-4) and the compound (I-7) of the present invention and the comparative compound 1 to the comparative compound 3 were prepared as shown in Tale 2 below.

TABLE 2

|  |  | Composition of this invention | | | | | | Comparative composition | | | | |
|---|---|---|---|---|---|---|---|---|---|---|---|---|
| Composition (% by weight) | | Example 10 | Example 11 | Example 12 | Example 13 | Example 14 | Example 15 | Comparative Example 1 | Comparative Example 2 | Comparative Example 3 | Comparative Example 4 | Comparative Example 5 |
| Mono-functional monomer | Compound (I-1) | 30 | | | | | | | | | | |
| | Compound (I-2) | | 30 | | | | | | | | | |
| | Compound (I-3) | | | 30 | | | | | | | | |
| | Compound (I-4) | | | | 30 | | | | | | | |
| | Compound (I-7) | | | | | 30 | | | | | | |
| | Compound (I-9) | | | | | | 30 | | | | | |
| | Comparative Compound 1 | | | | | | | 30 | | | 20 | |
| | Comparative Compound 2 | | | | | | | | 30 | | 10 | 10 |
| | Comparative Compound 3 | | | | | | | | | 30 | | 20 |
| Di-functional monomer | Compound VI | 28 | 28 | 28 | 28 | 28 | 28 | 28 | 28 | 28 | 28 | 28 |
| | Compound VII | 25 | 25 | 25 | 25 | 25 | 25 | 25 | 25 | 25 | 25 | 25 |
| | Compound VIII | 14 | 14 | 14 | 14 | 14 | 14 | 14 | 14 | 14 | 14 | 14 |
| Chiral | Compound IX | 3 | 3 | 3 | 3 | 3 | 3 | 3 | 3 | 3 | 3 | 3 |

TABLE 3

| Composition | Transition temperature | | | | Refractive index anisotropy |
|---|---|---|---|---|---|
| Example 10 | C | <20 | N* 113 | I | 0.158 |
| Example 11 | C | <20 | N* 109 | I | 0.155 |
| Example 12 | C | <20 | N* 168 | I | 0.173 |
| Example 13 | C | <20 | N* 131 | I | 0.170 |
| Example 14 | C | <20 | N* 94 | I | 0.155 |
| Example 15 | C | <20 | N* 104 | I | 0.175 |
| Comparative Example 1 | C | <20 | N* 120 | I | 0.159 |
| Comparative Example 2 | C | <20 | N* 124 | I | 0.180 |
| Comparative Example 3 | C | <20 | N* 119 | I | 0.155 |
| Comparative Example 4 | C | <20 | N* 121 | I | 0.166 |
| Comparative Example 5 | C | <20 | N* 123 | I | 0.164 |

Examples 16 to 21, Comparative Examples 6 to 10

Next, 2% of photopolymerization initiator Irgacure 907 (manufactured by Ciba Specialty Chemicals Inc.) was added to 98% of each of polymerizable liquid crystal compositions of the present invention of Example 10 to Example 15 and comparative compositions of Comparative Example 1 to Comparative Example 5, and then the resultant mixture was dissolved in cyclohexanone and applied on glass having polyimide by spin coating. Then, each of the mixtures was irradiated with ultraviolet light of 4 mW/cm$^2$ for 120 seconds using a high-pressure mercury lamp, producing each of polymers of the present invention of Example 16 to Example 21 and comparative polymers of Comparative Example 6 to Comparative Example 10. The haze values and appearances of the resultant polymers were evaluated. A haze value is represented by formula below, Haze (%)=$Td/Tt$×100

(wherein Td represents diffuse transmittance, and Tt represents total light transmittance), and was measured at 5 positions on a substrate using a haze meter (NHD2000 manufactured by Nippon Denshoku Industries Co., Ltd.) and averaged. Also, according to visual observation, a polymer which was entirely uniform without unevenness or the like was evaluated as "Good", and a polymer on which unevenness was observed was evaluated as "Uneven".

In any one of Example 16 to Example 21 containing the compound (I-1) to the compound (I-4), the compound (I-7), and the compound (I-9) of the present invention, a polymer having a small haze value and uniformity with no occurrence of unevenness was produced. On the other hand, in Comparative Example 6 and Comparative Example 8 containing the comparative compound 1 and the comparative compound 3, respectively, a polymer having a large haze value and nonuniformity with white striped unevenness caused thereon was produced. Comparative Example 7 containing the comparative compound 2 showed a small haze value and no unevenness, but Comparative Example 2 showed a refractive index anisotropy of as large as 0.180 as shown in Table 3 described above.

Therefore, it is found that all the compounds of the present invention have high storage stability as compared with the comparative compound 1 and the comparative compound 3 having the same degree of refractive index anisotropy as the present invention, and show low haze values and no unevenness and thus have high alignment properties when formed into polymers. It is also found that even as compared with a case (Comparative Examples 4 and 5) in which refractive index anisotropy was adjusted by adding each of the comparative compounds 1 and 3 to the comparative compound 2 having large refractive index anisotropy, the compounds of the present invention show low haze values and no unevenness and thus have high alignment properties when formed into polymers (Comparative Examples 9 and 10).

TABLE 4

| Polymer | Composition used | Haze value | Appearance |
|---|---|---|---|
| Example 16 | Example 10 | 1.1 | Good |
| Example 17 | Example 11 | 1.2 | Good |
| Example 18 | Example 12 | 1.5 | Good |
| Example 19 | Example 13 | 1.3 | Good |
| Example 20 | Example 14 | 1.2 | Good |
| Example 21 | Example 15 | 1.1 | Good |
| Comparative Example 6 | Comparative Example 1 | 3.5 | Slightly uneven |
| Comparative Example 7 | Comparative Example 2 | 1.6 | Good |
| Comparative Example 8 | Comparative Example 3 | 5.6 | Slightly uneven |
| Comparative Example 9 | Comparative Example 4 | 2.0 | Slightly uneven |
| Comparative Example 10 | Comparative Example 5 | 3.4 | Slightly uneven |

*Appearance: Good, Slightly uneven, Significantly uneven

The invention claimed is:

1. A polymerizable compound represented by general formula (I), $$P \text{—} (S^1 \text{—} X^1)_n \text{—} (A^1 \text{—} Z^1)_m \text{—} A^2 \text{—} Z^2 \text{—} A^3 \text{—} R^1 \qquad (I)$$

wherein P represents a substituent selected from polymerizable groups represented by formulae (P-1) to (P-15) below,

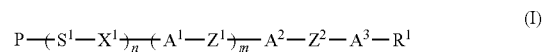

(P-1)

(P-2)

(P-3)

(P-4)

(P-5)

(P-6)

(P-7)

-continued

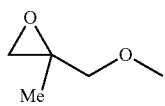 (P-8)

 (P-9)

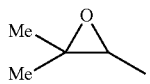 (P-10)

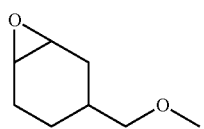 (P-11)

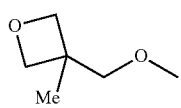 (P-12)

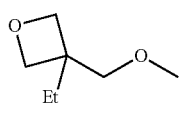 (P-13)

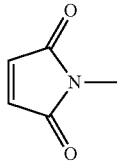 (P-14)

HS— (P-15)

$S^1$ represents an alkylene group having 1 to 20 carbon atoms, in which one —CH$_2$— or unadjacent two or more —CH$_2$— may be each independently substituted by —O—, or a single bond, and when a plurality of $S^1$ is present, $S^1$ may be the same or different; $X^1$ represents —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH$_2$CH$_2$—, —CH$_2$CF$_2$—, —CF$_2$CH$_2$—, —CF$_2$CF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CY$^1$=CY$^2$—, —C≡C—, or a single bond, wherein $Y^1$ and $Y^2$ each independently represent a hydrogen atom, an alkyl group having 1 to 12 carbon atoms, a fluorine atom, a chlorine atom, or a cyano group, and when a plurality of $X^1$ is present, $X^1$ may be the same or different; n represents 0, 1, 2, 3, or 4; $A^1$ and $A^2$ each independently represent a 1,4-phenylene group, a naphthalene-2,6-diyl group, a 1,4-cyclohexylene group, a 1,4-cyclohexenylene group, a 1,4-bicyclo[2.2.2]octylene group, a decahydronaphthalene-2,6-diyl group, a 1,2,3,4-tetrahydronaphthalene-2,6-diyl group, a pyridine-2,6-diyl group, a pyrimidine-2,5-diyl group, or a 1,3-dioxane-2,5-diyl group, which may be unsubstituted or substituted by a fluorine atom, a chlorine atom, a cyano group, a nitro group, an alkyl group having 1 to 7 carbon atoms, an alkoxy group having 1 to 7 carbon atoms, or an alkanoyl group having 1 to 7 carbon atoms; at least one hydrogen atom of the alkyl group, the alkoxy group, or the alkanoyl group may be substituted by a fluorine atom or chlorine atom, and when a plurality of $A^1$ is present, $A^1$ may be the same or different; $A^3$ represents a group selected from groups represented by formula ($A^3$-1) to formula ($A^3$-8) below,

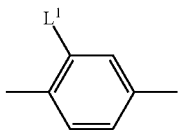 ($A^3$-1)

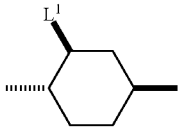 ($A^3$-2)

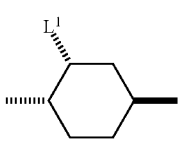 ($A^3$-3)

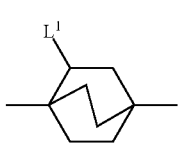 ($A^3$-4)

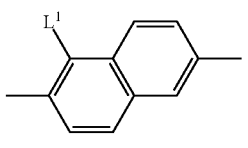 ($A^3$-5)

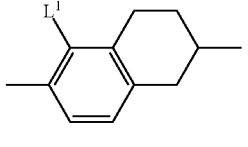 ($A^3$-6)

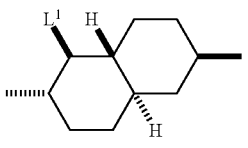 ($A^3$-7)

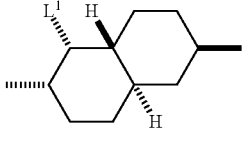 ($A^3$-8)

wherein $L^1$ represents an alkyl group having 1 to 7 carbon atoms, in which at least one hydrogen atom may be substituted by a fluorine atom or a chlorine atom, one —CH= or unadjacent two —CH= in a group represented by the formula ($A^3$-1) may be substituted by —N=, one —CH$_2$— or unadjacent two —CH$_2$— in groups represented by the formula ($A^3$-2) and formula ($A^3$-3) may be substituted by —O— or —S—, groups represented by the formula ($A^3$-1) to the formula ($A^3$-8) may be further substituted by a fluorine atom, a chlorine atom, a cyano group, a nitro group, or an alkyl group, alkoxy group, or alkanoyl group having 1 to 7 carbon atoms, in which at least one hydrogen atom may be substituted by a fluorine atom or chlorine atom; $Z^1$ and $Z^2$ each independently represent —OCH$_2$—, —CH$_2$O—, —COO—, —OCO—, —CO—S—, —S—CO—, —CO—NH—, —NH—CO—, —SCH$_2$—, —CH$_2$S—, —CF$_2$O—, —OCF$_2$—, —CF$_2$S—, —SCF$_2$—, —CH$_2$CH$_2$—, —CH$_2$CF$_2$—, —CF$_2$CH$_2$—, —CF$_2$CF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —COO—CH$_2$—, —CH$_2$—COO—, —CH$_2$—OCO—, —CY$^3$=CY$^4$—, or a single bond wherein Y$^3$ and Y$^4$ each independently represent a hydrogen atom, an alkyl group having 1 to 12 carbon atoms, a fluorine atom, a chlorine atom, or a cyano group, and when a plurality of $Z^1$ is present, $Z^1$ may be the same or different; $R^1$ represents a fluorine atom, a chlorine atom, a cyano group, or an alkyl group having 1 to 12 carbon atoms, at least one hydrogen atom in the alkyl group may be substituted by a fluorine atom, a chlorine atom, or a cyano group; and m represents 0, 1, 2, 3, or 4, wherein a polymer obtained by polymerizing the polymerizable compound has a haze value of 1.1 to 1.5.

2. The polymerizable compound according to claim 1, wherein in the general formula (1), $A^3$ is represented by the formula ($A^3$-1) or the formula ($A^3$-5) in which $L^1$ represents a fluorine atom, a chlorine atom, or an alkyl group or alkoxy having 1 to 4 carbon atoms, and a hydrogen atom on a benzene ring or naphthalene ring may be substituted by a fluorine atom, a chlorine atom, or an alkyl group or alkoxy group having 1 to 4 carbon atoms.

3. The polymerizable compound according to claim 1, wherein in the general formula (1), $A^3$ is represented by the formula ($A^3$-1) or the formula ($A^3$-5) in which $L^1$ represents a fluorine atom, a chlorine atom, a CH$_3$ group, or a CH$_3$O group, and a hydrogen atom on a benzene ring or naphthalene ring may be substituted by a fluorine atom, a chlorine atom, a CH$_3$ group, or a CH$_3$O group.

4. The polymerizable compound according to claim 1, wherein in the general formula (1), $Z^1$ and $Z^2$ each independently represent —COO—, —OCO—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, or —CH$_2$—OCO—.

5. A polymerizable liquid crystal composition containing the polymerizable compound according to claim 1.

6. A polymer produced by polymerizing the polymerizable liquid crystal composition according to claim 5.

7. The optically anisotropic body comprising the polymer according to claim 6.

* * * * *